United States Patent
Tuteja et al.

(10) Patent No.: US 10,493,037 B2
(45) Date of Patent: Dec. 3, 2019

(54) MULTIPHASIC PARTICLES FABRICATED BY WETTABILITY ENGENDERED TEMPLATED SELF-ASSEMBLY (WETS) METHODS

(71) Applicant: THE REGENTS OF THE UNIVERSITY OF MICHIGAN, Ann Arbor, MI (US)

(72) Inventors: Anish Tuteja, Ann Arbor, MI (US); Sai Pradeep Reddy Kobaku, Ann Arbor, MI (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 62 days.

(21) Appl. No.: 15/544,842

(22) PCT Filed: Jan. 19, 2016

(86) PCT No.: PCT/US2016/013828
§ 371 (c)(1),
(2) Date: Jul. 19, 2017

(87) PCT Pub. No.: WO2016/118464
PCT Pub. Date: Jul. 28, 2016

(65) Prior Publication Data
US 2018/0353433 A1    Dec. 13, 2018

Related U.S. Application Data

(60) Provisional application No. 62/105,026, filed on Jan. 19, 2015.

(51) Int. Cl.
*A61K 9/50* (2006.01)
*B82Y 30/00* (2011.01)
(Continued)

(52) U.S. Cl.
CPC ............ *A61K 9/5089* (2013.01); *A61K 9/501* (2013.01); *A61K 9/5015* (2013.01);
(Continued)

(58) Field of Classification Search
None
See application file for complete search history.

(56) References Cited

U.S. PATENT DOCUMENTS

| 6,348,542 B1 | 2/2002 | Naruse et al. |
| 6,596,296 B1 | 7/2003 | Nelson et al. |

(Continued)

FOREIGN PATENT DOCUMENTS

| WO | 2007024323 A2 | 3/2007 |
| WO | WO-2009042231 A2 | 4/2009 |

(Continued)

OTHER PUBLICATIONS

A Walther, AHE Muller. "Janus Particles: Synthesis, Self-Assembly, Physical Properties, and Applications." Chemical Reviews, vol. 113, 2013, pp. 5194-5261. (Year: 2013).*

(Continued)

*Primary Examiner* — Isaac Shomer
(74) *Attorney, Agent, or Firm* — Harness, Dickey & Pierce, P.L.C.

(57) ABSTRACT

Methods for forming multiphasic microparticles by using wettability engendered template self-assembly (WETS) techniques are provided. A template is used that defines wettable regions to polar and non-polar liquids and non-wettable regions to polar and non-polar liquids. A first liquid is applied to the template and forms a solid or semi-solid release layer. A second liquid is applied over the release layer to form a solid or semi-solid first layer and a third liquid is applied over the first layer to form a solid or semi-solid second layer. The first layer and the second layer (Continued)

can be released from the template by removing the release layer from the template with a treatment agent to form multiphasic microparticles. Methods for making the templates and multiphasic micro particles are also provided.

26 Claims, 18 Drawing Sheets

(51) Int. Cl.
    *B01J 2/00*         (2006.01)
    *A61K 9/51*       (2006.01)
    *B82Y 5/00*       (2011.01)

(52) U.S. Cl.
    CPC .......... *A61K 9/5026* (2013.01); *A61K 9/5031* (2013.01); *A61K 9/5036* (2013.01); *A61K 9/5042* (2013.01); *A61K 9/5057* (2013.01); *A61K 9/5073* (2013.01); *A61K 9/5115* (2013.01); *A61K 9/5123* (2013.01); *A61K 9/5138* (2013.01); *A61K 9/5146* (2013.01); *A61K 9/5161* (2013.01); *A61K 9/5169* (2013.01); *A61K 9/5192* (2013.01); *B01J 2/003* (2013.01); *B82Y 30/00* (2013.01); *B82Y 5/00* (2013.01)

(56) References Cited

U.S. PATENT DOCUMENTS

| | | | |
|---|---|---|---|
| 8,153,233 | B2 | 4/2012 | Sheng et al. |
| 9,186,631 | B2 | 11/2015 | Tuteja et al. |
| 9,394,408 | B2 | 7/2016 | Ramirez et al. |
| 9,650,518 | B2 | 5/2017 | Meuler et al. |
| 9,765,255 | B2 | 9/2017 | Guenthner et al. |
| 2004/0223926 | A1 | 11/2004 | Kobayashi |
| 2006/0201390 | A1* | 9/2006 | Lahann .................. B82Y 10/00 106/401 |
| 2007/0166513 | A1 | 7/2007 | Sheng et al. |
| 2007/0232169 | A1 | 10/2007 | Strickler et al. |
| 2008/0241512 | A1 | 10/2008 | Boris et al. |
| 2009/0246142 | A1 | 10/2009 | Bhatia et al. |
| 2010/0038830 | A1* | 2/2010 | Lahann .................. B82Y 10/00 264/484 |
| 2010/0316842 | A1 | 12/2010 | Tuteja et al. |
| 2011/0033663 | A1 | 2/2011 | Svec et al. |
| 2011/0077172 | A1 | 3/2011 | Aizenberg et al. |
| 2012/0009267 | A1 | 1/2012 | Cho et al. |
| 2014/0017457 | A1 | 1/2014 | Megaridis et al. |
| 2014/0147510 | A1 | 5/2014 | Lahann et al. |
| 2015/0136606 | A1 | 5/2015 | Tuteja et al. |
| 2016/0129400 | A1 | 5/2016 | Tuteja et al. |
| 2016/0251803 | A1 | 9/2016 | Tuteja et al. |
| 2016/0281007 | A1 | 9/2016 | Reams et al. |

FOREIGN PATENT DOCUMENTS

| | | | |
|---|---|---|---|
| WO | 2009111437 A2 | 9/2009 | |
| WO | 2011/159699 A2 | 12/2011 | |
| WO | 2012/058464 A2 | 5/2012 | |
| WO | 2013/173722 A2 | 11/2013 | |
| WO | WO-2014047477 A2 * | 3/2014 | ........... A61K 31/433 |
| WO | 2015/054406 A1 | 4/2015 | |

OTHER PUBLICATIONS

H Zhang, JK Nunes, SEA Gratton,m KP Herlihy, PD Pohlhaus, JM DeSimone. "Fabrication of multiphasic and regio-specifically functionalized PRINT® particles of controlled size and shape." New Journal of Physics, vol. 11, 2009, 075018, pp. 1-16. (Year: 2009).*

H Zhang, JK Nunes, SEA Gratton, KP Herlihy, PD Pohlhaus, JM DeSimone. "Fabrication of multiphasic and regio-specifically functionalized PRINT particles of controlled size and shape." New Journal of Physics, vol. 11, 2009, article 075018, pp. 1-16. (Year: 2009).*

JM DeSimone, J-Y Wang, Y Wang. "Chapter 5 Particle Replication in Non-wetting Templates: a Platform for Engineering Shape-and Size-specific Janus Particles." From the book "Janus Particle Synthesis, Self-Assembly and Applications." The Royal Society of Chemistry, 2012, pp. 90-107. (Year: 2012).*

Zhang, H. et al. "Fabrication of multiphasic and regio-specifically functionalized PRINT® particles of controlled size and shape." New Journal of Physics. vol. II. Article No. 075018. pp. 1-16 (2009).

Van, T. N. et al. "Tuning Hydrophobicity of TiO2 Layers with Silanization and Self- Assembled Nanopatterning" Langmuir. vol. 29. pp. 3054-3060 (2013).

Kobaku, S.P.R. et al. "Patterned superomniphobic-superomniphilic surfaces: Templates for site-selective self-assembly." Angewandte Chemie International Edition. 51. pp. 10109-10113 (2012).

Lee, M.J. et al. "Nanoparticle assembly into a patterned template by controlling the surface wettability." Nanotechnology. 19. p. 355301 (2008).

Zhao, B. et al. "Surface-directed liquid flow inside microchannels." Science. 291. pp. 1023-1026 (2001).

Huang, Z.Y. et al. "Selective deposition of conducting polymers on hydroxyl-terminated surfaces with printed monolayers of alkylsiloxanes as templates." Langmuir. 13. pp. 6480-6484. (1997).

Lai, Y.K. et al. "Bioinspired patterning with extreme wettability contrast on TiO2 nanotube array surface: A versatile platform for biomedical applications," Anal Chem. 81. pp. 7091-7095 (2013).

Sehgal, A. et al. "From finite-amplitude equilibrium structures to dewetting in thin polymer films on chemically patterned substrates." Soft Matter. 8. p. 10394 (2012).

Lee, S. et al. "Site-selective assembly and fixation of colloidal particles into two-dimensional array on wettability-patterned surface." Japanese Journal of Applied Physics. 46(2). pp. 45-49 (2007).

Masuda, Y. "Morphology Control, Self-Assembly and Site-Selective Deposition of Nanocrystals." Nanocrystals. InTech. pp. 1-30 (2010).

Lai, Y. et al. "Bioinspired TiO2 nanostructure films with special wettability and adhesion for droplets manipulation and patterning," Scientific Reports. 3. 3009 (2013).

Moore N.C. "A material that most liquids won't wet." (2013).

Lim. "UV-Driven Reversible Switching of a Roselike Vanadium Oxide Film between Superhydrophobicity and Superhydrophilicity." J. Am. Chem. Soc. 129. 4128-4129 (2007).

International Search Report dated Aug. 17, 2016 in International PCT Application No. PCT/US2016/013828 (WO2016/118464).

Written Opinion dated Aug. 17, 2016 in International PCT Application No. PCT/US2016/013828 (WO2016/118464).

Extended European Search Report and Opinion for European Patent Application No. 16740562.0 dated Jun. 11, 2018, 5 pages.

* cited by examiner

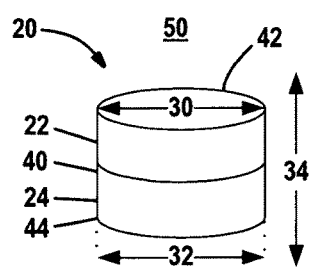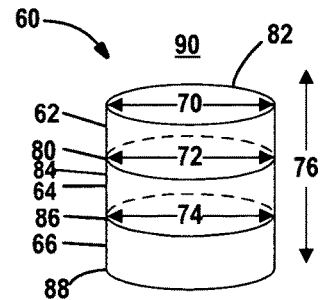
FIG. 1
FIG. 2
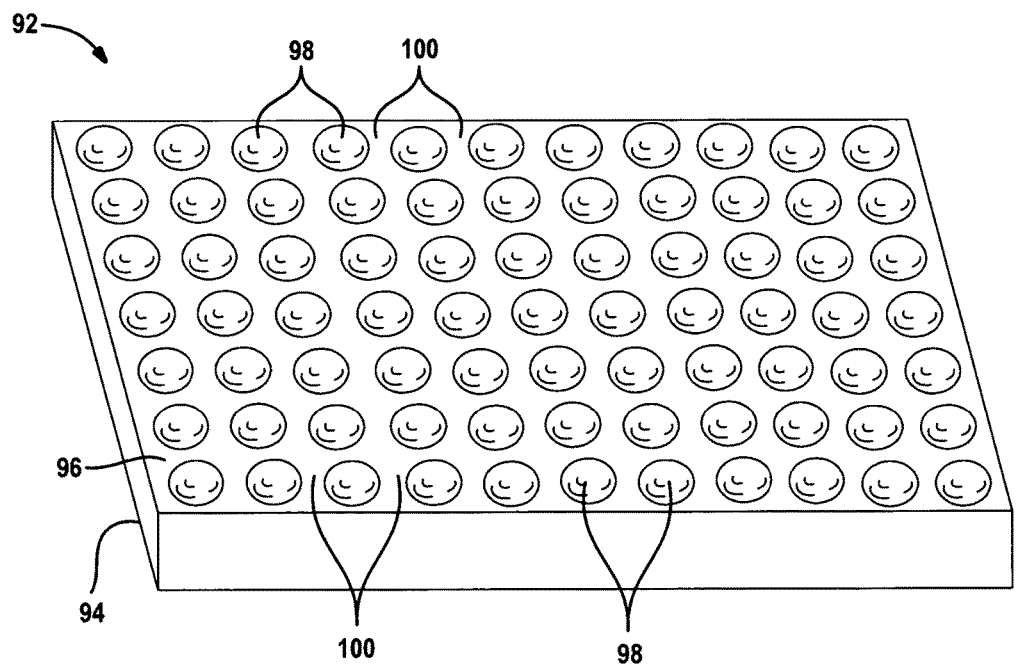
FIG. 3

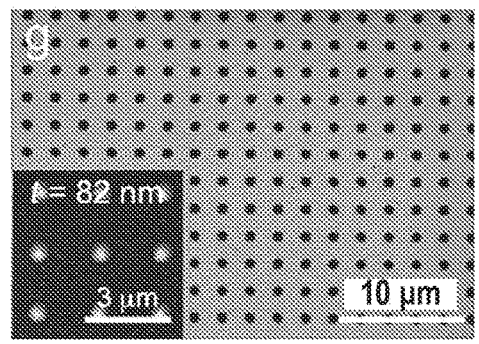
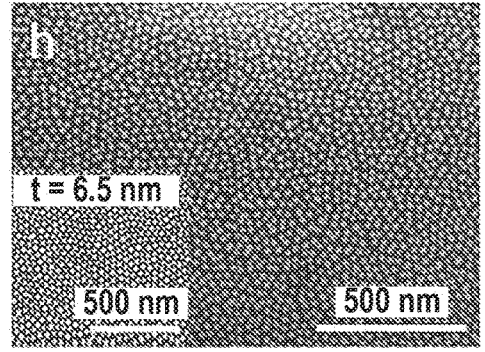
FIG. 7G              FIG. 7H
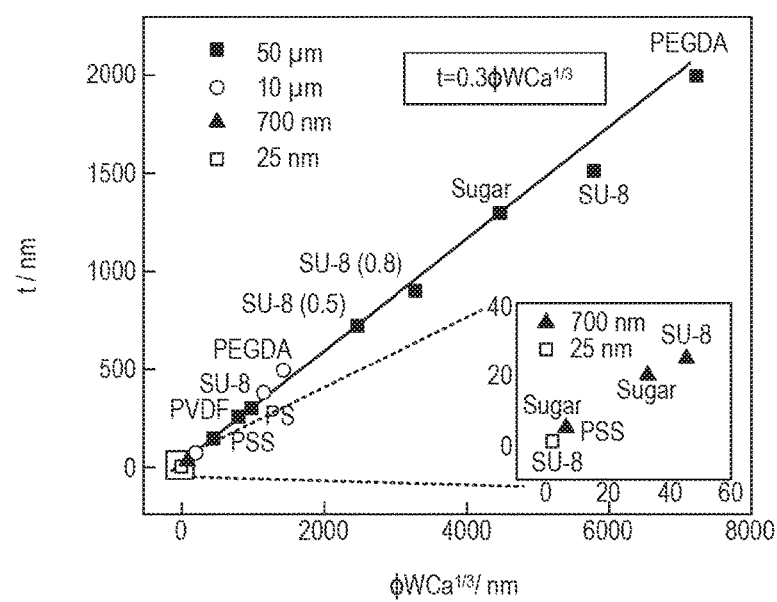
FIG. 7I

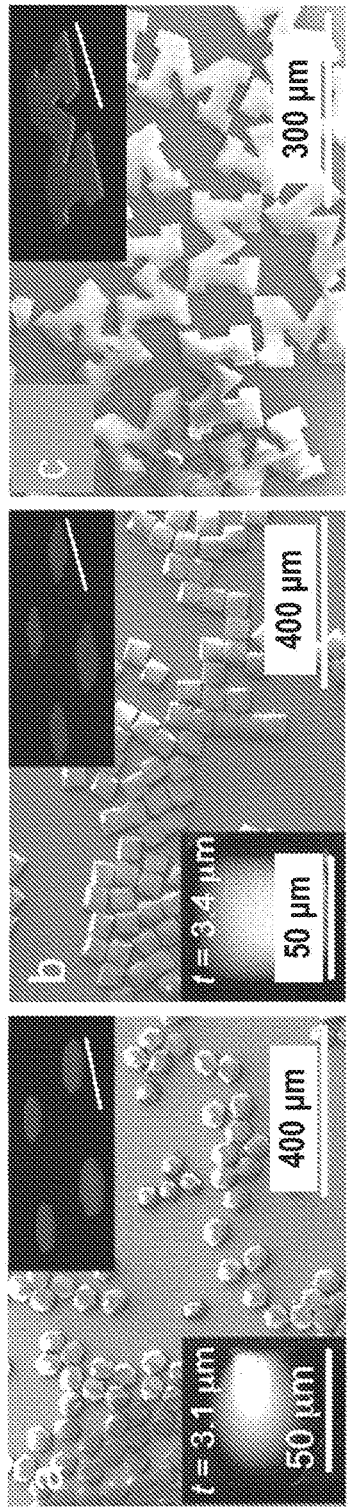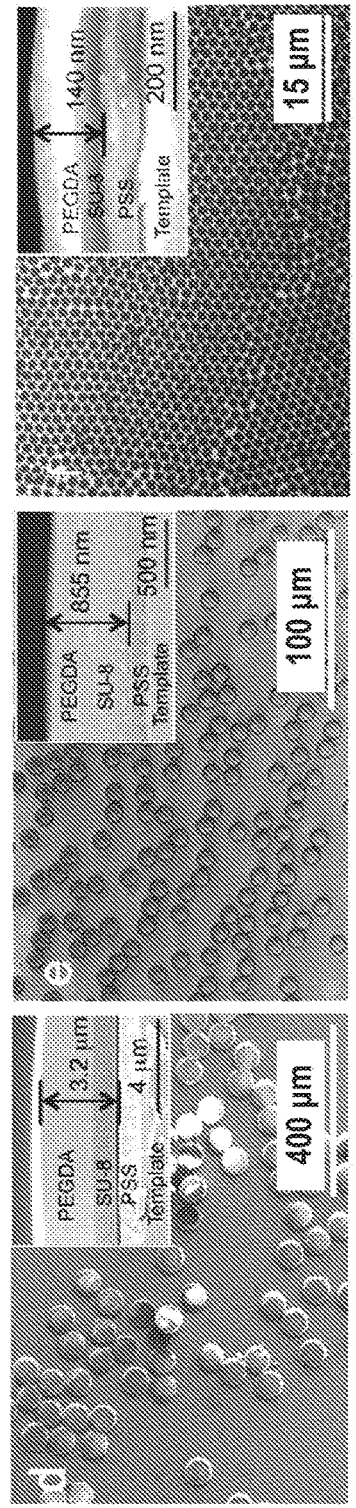
FIG. 11A  FIG. 11B  FIG. 11C
FIG. 11D  FIG. 11E  FIG. 11F

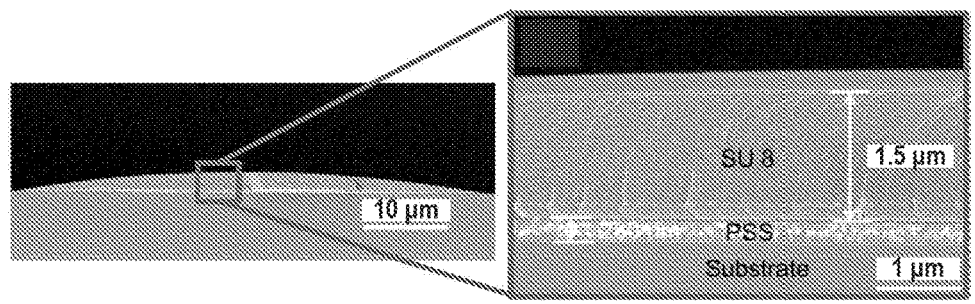
FIG. 13A
FIG. 13B
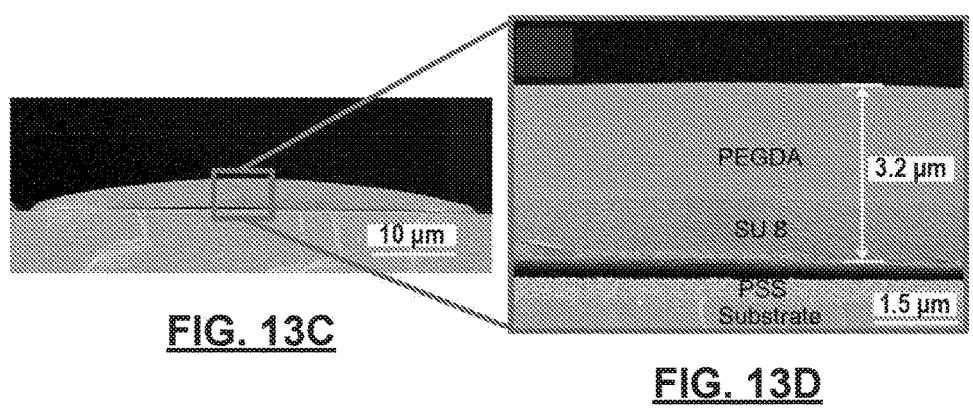
FIG. 13C
FIG. 13D
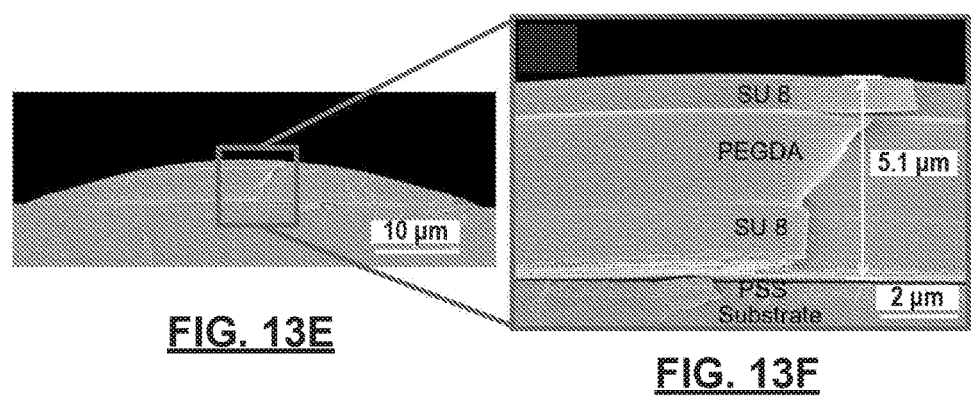
FIG. 13E
FIG. 13F
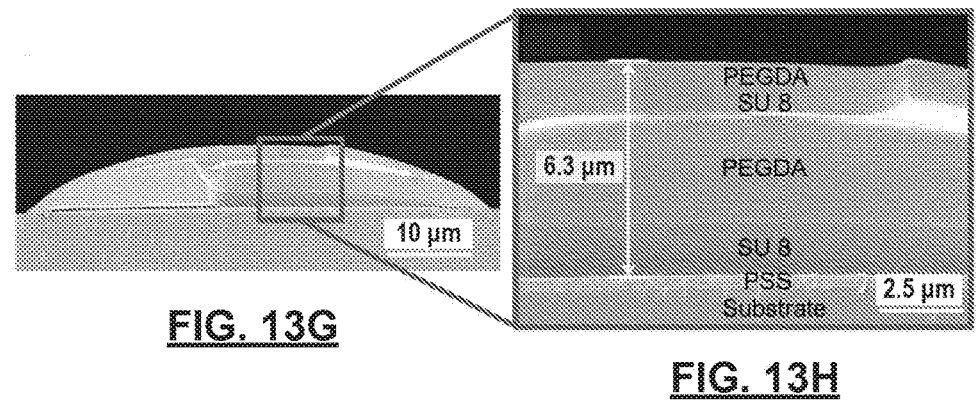
FIG. 13G
FIG. 13H

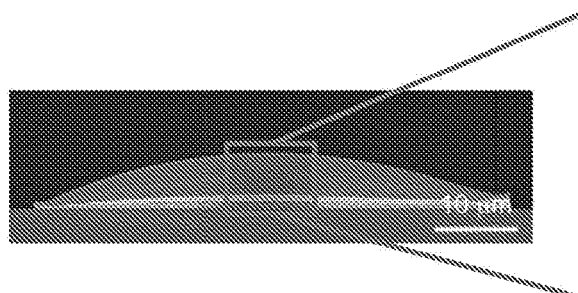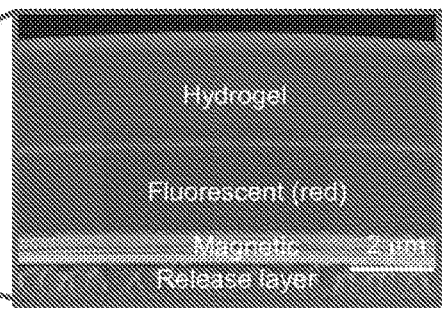
FIG. 14A
FIG. 14B
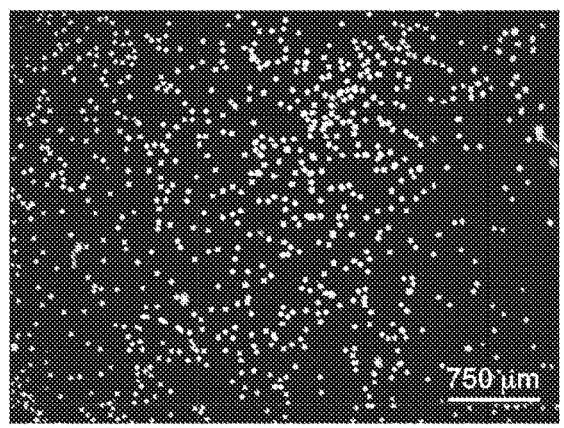
FIG. 14C
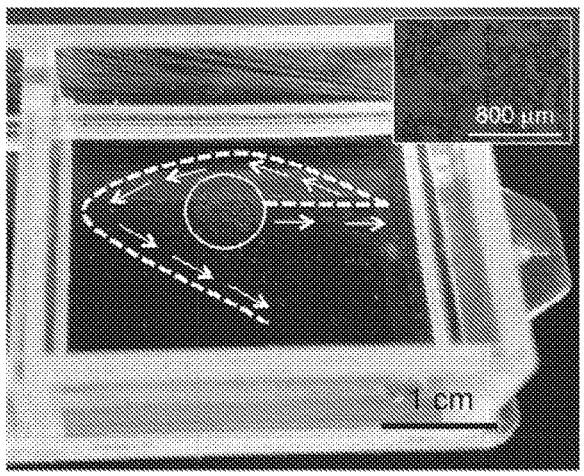
FIG. 14D

MULTIPHASIC PARTICLES FABRICATED BY WETTABILITY ENGENDERED TEMPLATED SELF-ASSEMBLY (WETS) METHODS

CROSS-REFERENCE TO RELATED APPLICATIONS

This application is a 371 National Phase of PCT/US2016/013828 filed Jan. 19, 2016 which claims the benefit of U.S. Provisional Application No. 62/105,026, filed on Jan. 19, 2015. The entire disclosures of the above applications are incorporated herein by reference.

FIELD

The present disclosure relates to processes for fabricating multiphasic particles by using wettability engendered template self-assembly (WETS) techniques and multiphasic particles made therefrom.

BACKGROUND

This section provides background information related to the present disclosure which is not necessarily prior art.

Microparticles and nanoparticles can be used in a variety of applications, including biotherapeutics and vaccines, as well as biological sensors, optical devices and nanomotors, by way of non-limiting example. In recent years, nanoparticles have been developed to carry drugs for treatment of diseases like cancer and diabetes, but can also be used for a variety of other functions, including detecting disease. Nanoparticle-based therapeutics can be administered orally as a pill or an inhalant. However, nanoparticles need to have very particular shape, size and composition in order to successfully enter the blood stream or target the area of disease within a patient. Thus, precise control over the geometry and chemistry of multiphasic micro- and nano-particles is of importance for a wide range of applications including drug delivery, vaccines and inhalation biotherapeutics, and biological sensors, among others.

The production of uniformly sized micro- and nano-particles has been difficult and remained problematic for current manufacturing processes. The development of micro- or nano-particle synthesis techniques, which result in such particles having tightly controlled size, shape and composition remains a technical challenge. Further, in a bottom-up approach envisioned for building materials and devices of the future, it is necessary to develop precisely designed particles (building blocks) that can assemble in a preprogrammed manner to yield desired structures and properties. However, fabricated micro- or nanoparticles typically have a uniform distribution of all materials (isotropic). In order to design particles that self-assemble in a preprogrammed manner, it is important to control the size, shape, and distribution of dissimilar materials within each particle to form anisotropic particles, such as Janus, tri-phasic, or quad-phasic particles. Although, many different routes for synthesizing such multiphasic particles have been explored previously, it would be desirable to develop a simple, inexpensive technique for the fabrication of monodisperse, multiphasic particles of any desired composition and size, with precise control over particle geometry.

SUMMARY

This section provides a general summary of the disclosure, and is not a comprehensive disclosure of its full scope or all of its features.

In certain aspects, the present disclosure provides a method of forming multiphasic microparticles. The method of forming multiphasic microparticles may comprise applying a first liquid composition to a surface of a template. The template surface defines a first region having a first receding contact angle of less than or equal to about 5° for polar and non-polar liquids and a second region having a second receding contact angle of greater than or equal to about 10° for polar or non-polar liquids. The first liquid composition thus remains in the first region and forms a release layer that is a solid or semi-solid. Next, a second liquid composition is applied over the release layer. The second liquid composition remains in the first region and forms a first layer that is a solid or semi-solid. A third liquid composition may then be applied over the first layer. The third liquid composition remains in the first region and forms a second layer that is a solid or semi-solid. Finally, the first layer and the second layer can be released from the template by removing the release layer from the template to create a multiphasic microparticle comprising at least the first layer and the second layer.

Methods for forming a template for forming multiphasic microparticles are also provided. Such a method may comprise applying a metal oxide material selected from a group consisting of: titanium oxide ($TiO_2$), zinc oxide (ZnO), tin oxide ($SnO_2$), tungsten oxide ($WO_3$), vanadium oxide ($V_2O_5$), and combinations thereof to a substrate. Then, the metal oxide material may be silanized with a low surface energy fluorine-containing silane to form a non-wettable surface having a first receding contact angle greater than or equal to about 10° for polar and non-polar liquids. One or more select regions of the non-wettable surface are activated to form a wettable region having a second receding contact angle of less than or equal to about 5° for polar and non-polar liquids within the non-wettable surface. The wettable region is capable of receiving polar and non-polar liquid compositions to form layers of a multiphasic microparticle.

In other aspects, a multiphasic microparticle is provided. The multiphasic microparticle may comprise a first layer defining a first phase and a second layer defining a second phase. At least one of the first phase and the second phase comprises a polymer. In certain aspects, the first layer and the second layer may be respectively annealed. The first layer is stacked on the second layer, so that the first layer defines a first major lateral dimension and the second layer defines a second major lateral dimension. The first major lateral dimension and the second major lateral dimension are perpendicular to a major longitudinal dimension of the multiphasic microparticle. The major longitudinal dimension may be less than or equal to about 50 µm. Further, the multiphasic microparticle may have an aspect ratio of less than or equal to about 1.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 shows a schematic of an exemplary multiphasic particle (a biphasic particle) formed in accordance with certain aspects of the present disclosure.

FIG. 2 shows a schematic of an alternative variation of a multiphasic particle (a triphasic particle) formed in accordance with other aspects of the present disclosure.

FIG. 3 shows a schematic of an exemplary patterned surface of a template used to form multiphasic particles in accordance with certain aspects of the present disclosure.

Figure 7A:
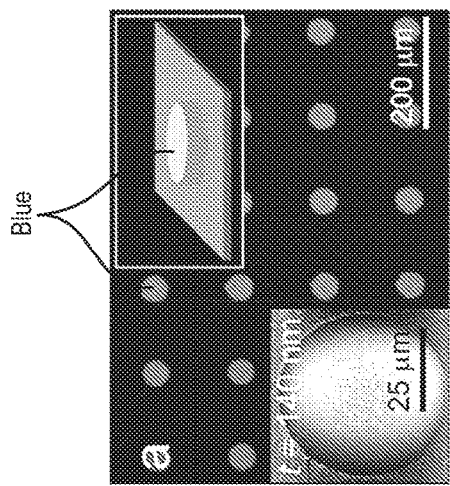
Figure 7B:
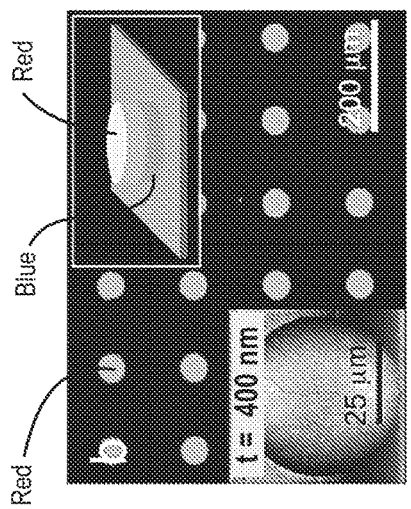
Figure 7C:
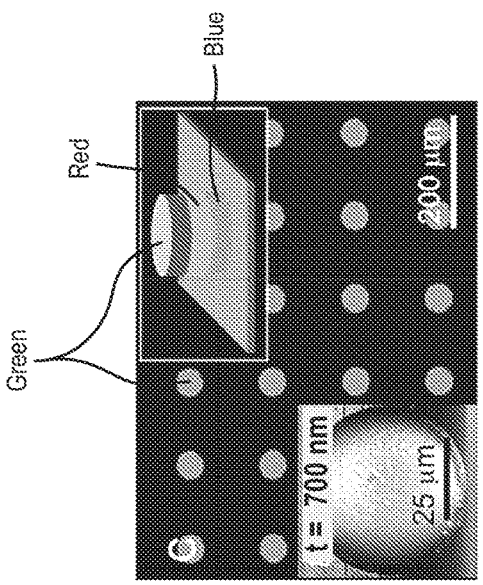
Figure 7D:
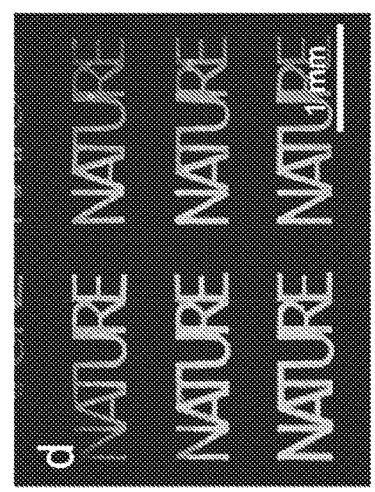
Figure 7E:
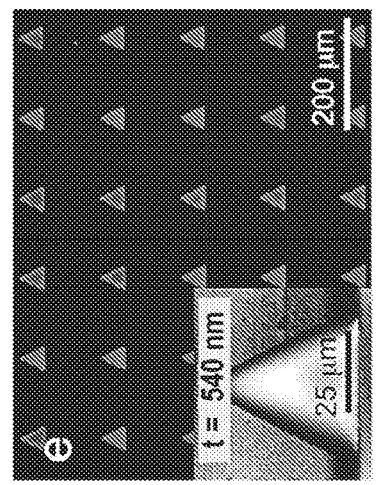
Figure 7F:
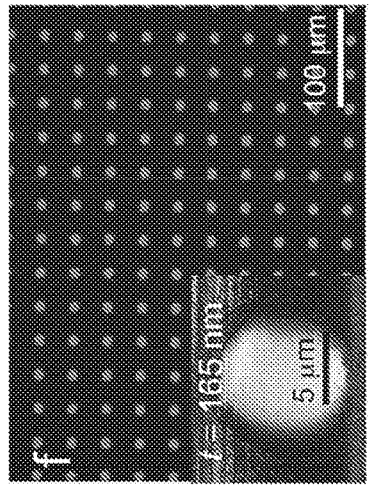

FIGS. 7A-7I. FIG. 7A shows a fluorescent micrograph of a sacrificial release layer comprising poly(sodium 4-styrenesulfonate) (PSS; dyed blue) formed on a template via wettability engendered assembly techniques of the present disclosure. FIG. 7B shows a first layer comprising poly(vinylidene fluoride) (PVDF; dyed red) formed on the sacrificial release layer comprising PSS in FIG. 7A in accordance with certain aspects of the present disclosure. FIG. 7C shows a second layer comprising polystyrene (PS; dyed green) formed in accordance with certain aspects of the present disclosure over the top of the first layer comprising PVDF and the release layer comprising PSS. The upper insets of FIGS. 7A-7C show schematics of each polymer layer formed on the high surface energy (or wettable) domains of the surface of the template, while the bottom insets in FIGS. 7A-7C show the corresponding AFM height images and the thickness (t) of the polymer assembly (thicknesses of 140 nm, 400 nm, and 700 nm in FIGS. 7A-7C). FIG. 7D shows a fluorescent micrograph of a patterned template with a PS polymer applied as a layer in the complex shaped wettable surface regions (a logo of "NATURE"). FIG. 7E shows a fluorescent micrograph of a patterned template with a PS polymer applied as a layer in the wettable surface regions having a triangular cross-sectional shape, so that triangular prisms are formed. FIG. 7F shows a fluorescent micrograph of a patterned template with monodisperse 10 μm domains of a deposited sacrificial release layer comprising PSS, a first layer comprising PVDF, and a second layer comprising PS in the following order: PSS-PVDF-PS. FIGS. 7E-7F also show AFM height images with thicknesses of 540 nm and 165 nm, respectively. FIGS. 7G-7H show SEM images of multiphasic particle assemblies on a template with a release layer, including the following layers: TiO$_2$-PSS-SU-8-PS and alternatively TiO$_2$-Sugar-SU-8-PS within the 700 nm and 25 nm high surface energy domains, respectively (where SU-8 is a negative epoxy photoresist). The bottom insets of FIGS. 7G-7H show the corresponding AFM height images and the thickness (t) of the multiphasic particle assembly. FIG. 7I shows a plot comparing the predicted (solid black line) and measured (individual data points) thicknesses for a variety of polymers deposited as layers. The thickness t for the polymer depositions within patterned domains is an average value across 30 domains.

Figure 8A:
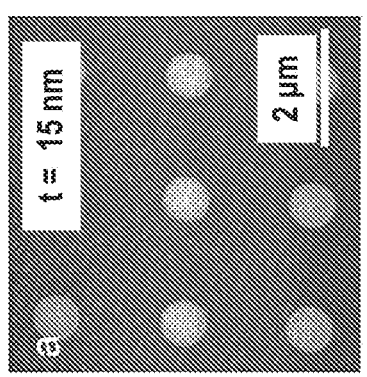
Figure 8B:
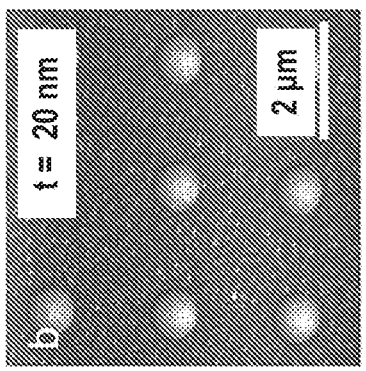
Figure 8C:
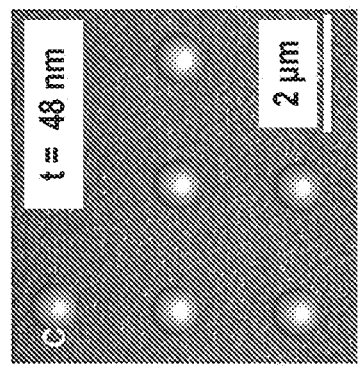
Figure 8D:
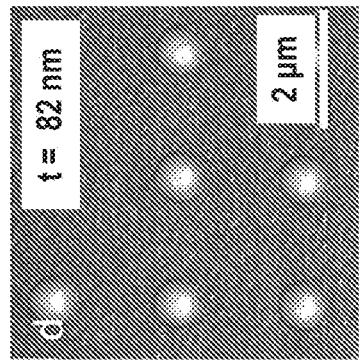
Figure 8E:
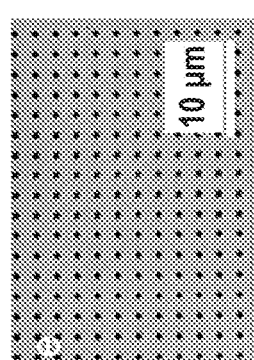
Figure 8F:
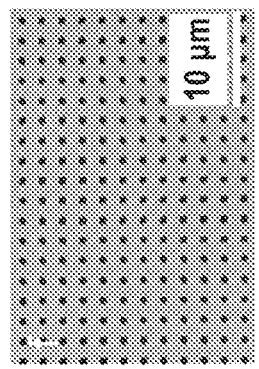
Figure 8G:
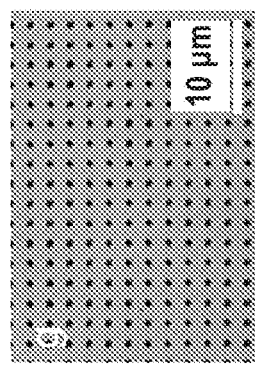
Figure 8H:
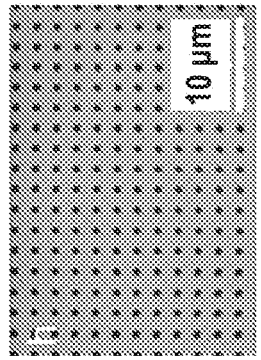

FIGS. 8A-8H show fabrication of 700 nm diameter multiphasic nanoparticles according to certain aspects of the present disclosure. The atomic force microscopy (AFM) height images and thickness t are provided. FIG. 8A shows high surface energy regions formed in silanized TiO$_2$ of a template. FIG. 8B shows PSS deposited on top of the wettable regions in the TiO$_2$. FIG. 8C shows a negative epoxy photoresist (SU-8) deposited on top of the PSS layer. FIG. 8D shows polystyrene (PS) deposited on top of the SU-8 and PSS layers. Corresponding SEM images include high surface energy TiO$_2$ domains (FIG. 8E corresponding to FIG. 8A), PSS deposited within the wettable domains (FIG. 8F corresponding to FIG. 8B), SU-8 deposited on top of PSS (FIG. 8G corresponding to FIG. 8C), and polystyrene deposited on top of SU-8 and PSS (FIG. 8H corresponding to FIG. 8D).

Figure 9A:
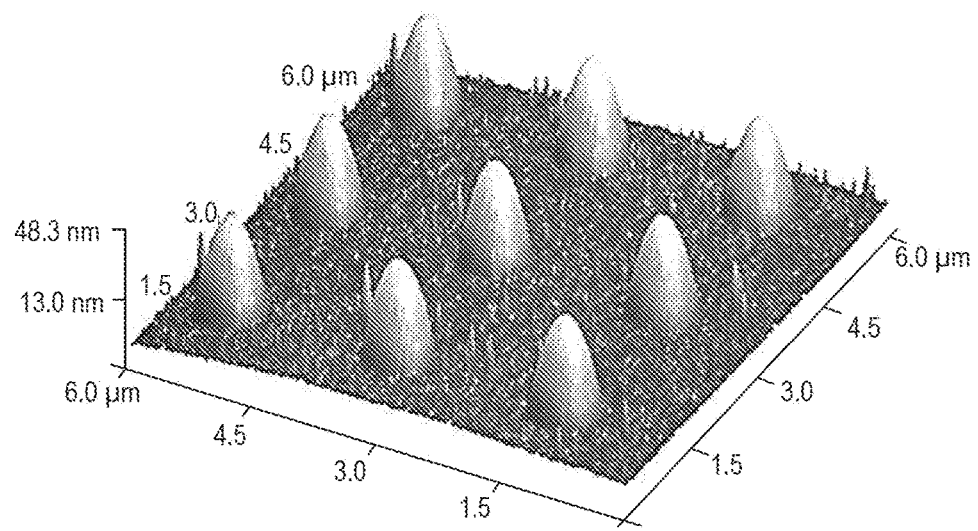
Figure 9B:
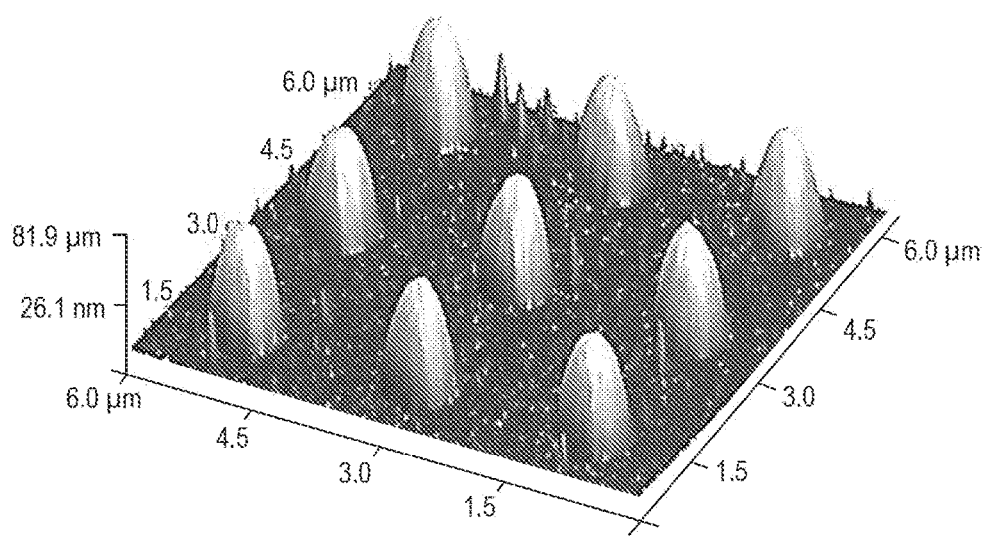
Figure 9C:
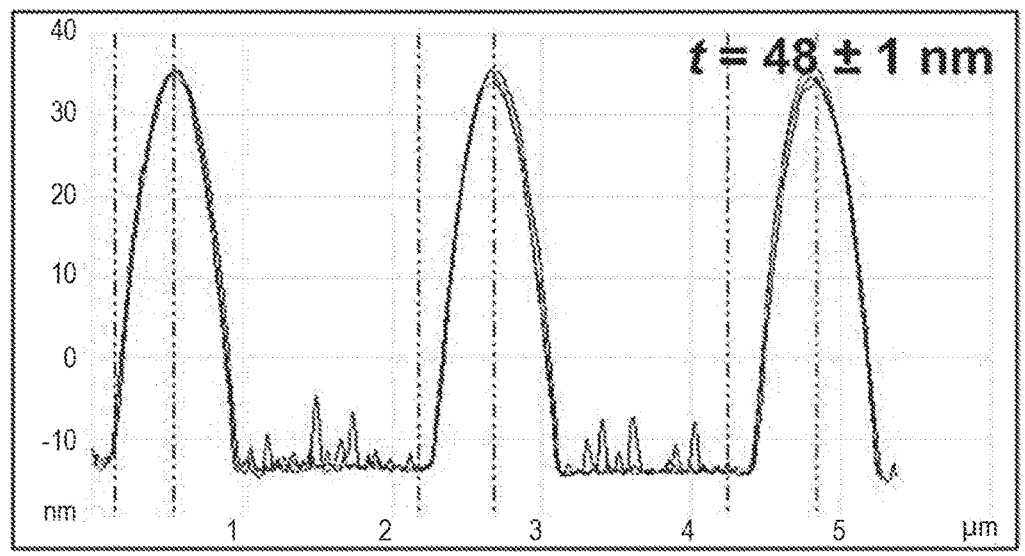
Figure 9D:
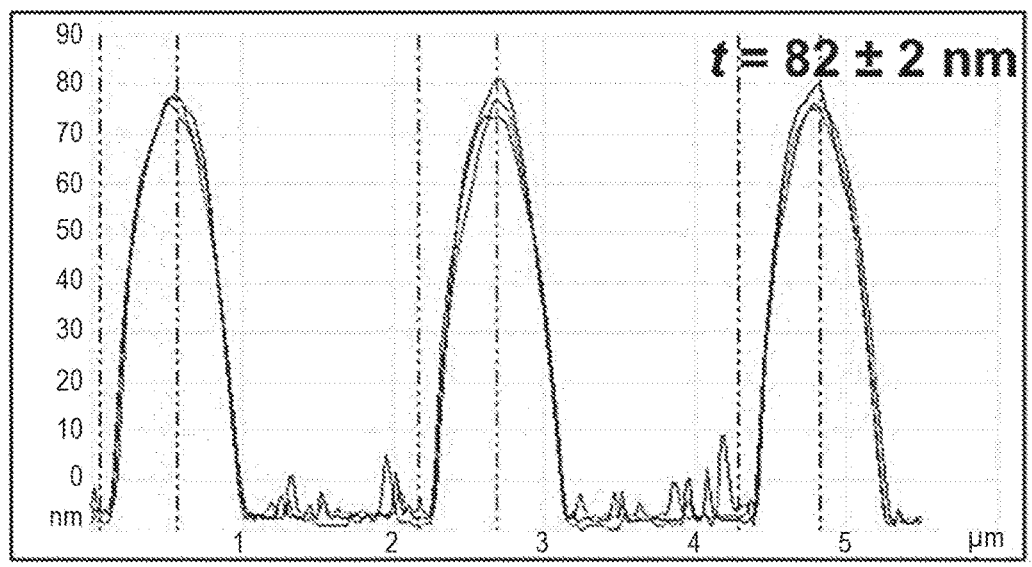

FIGS. 9A-9D show variation in thickness of polymer deposition layers prepared in accordance with certain aspects of the present disclosure across different 700 nm TiO$_2$ wettable domains. FIGS. 9A-9B show 3-Dimensional AFM height images of multi-phasic polymer assemblies shown in FIGS. 8C and 8D, respectively. FIGS. 9C and 9D show height scan profiles of the different polymer assemblies shown in FIGS. 9A and 9B, respectively.

Figure 10A:
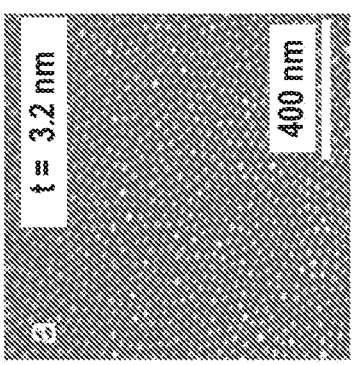
Figure 10B:
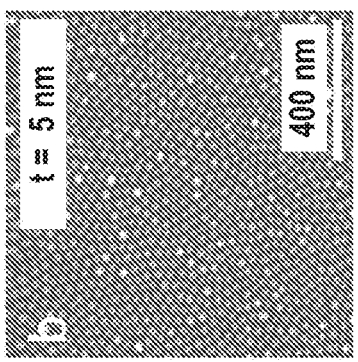
Figure 10C:
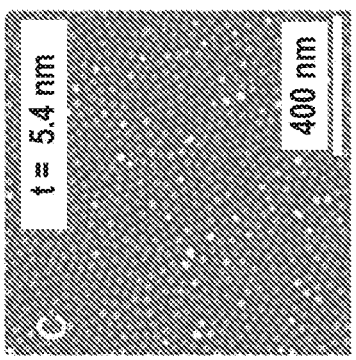
Figure 10D:
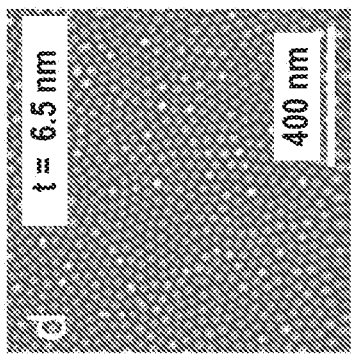
Figure 10E:
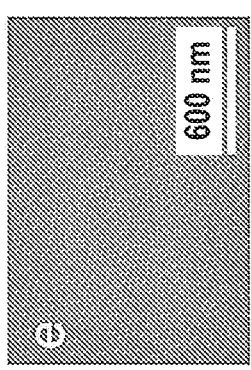
Figure 10F:
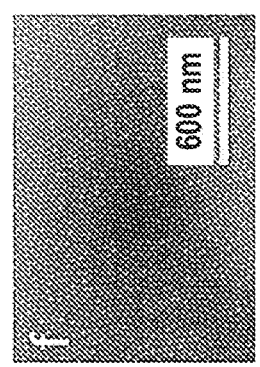
Figure 10G:
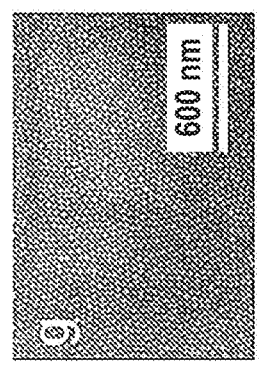
Figure 10H:
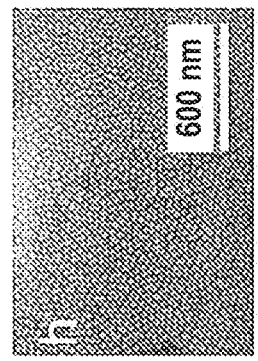

FIGS. 10A-10H show methods of forming multiphasic nanoparticles with an average diameter of about 25 nm according to certain aspects of the present disclosure. AFM height images are provided with a thickness "t." FIG. 10A shows high surface energy TiO$_2$ domains, while FIG. 10B shows sugar deposited on top of the wettable TiO$_2$ domains. FIG. 10C shows SU-8 deposited on top of the sugar layer. FIG. 10D shows polystyrene deposited on top of the layers of SU-8 and sugar. Corresponding SEM images are shown in FIG. 10E of high surface energy TiO$_2$ regions, FIG. 10F of sugar deposited within the wettable regions, FIG. 10G of SU-8 deposited on top of the sugar layer, and FIG. 10H of polystyrene deposited on top of SU-8 and sugar.

Figures 11G, 11H, 11I:
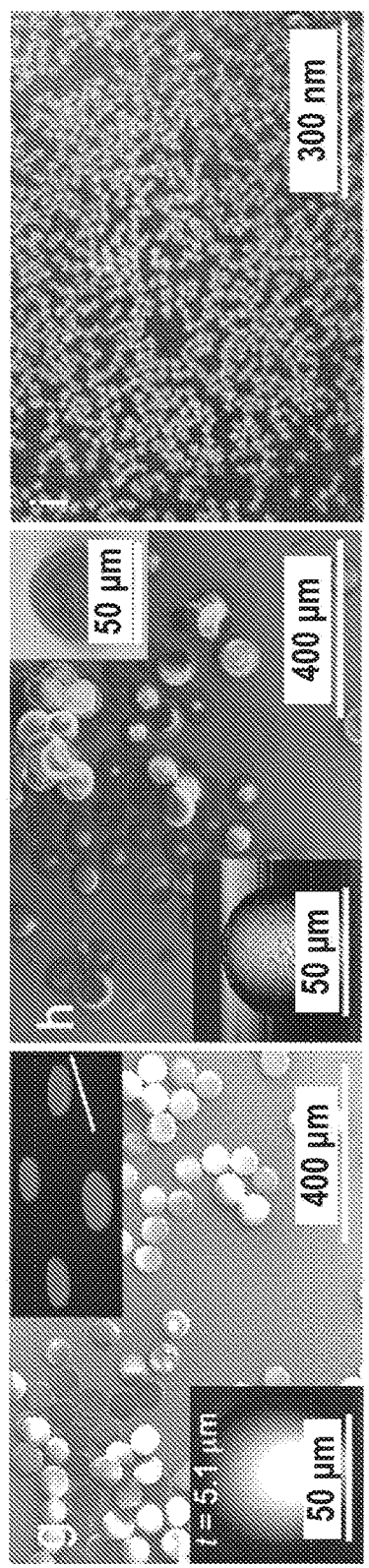

FIGS. 11A-11I show multi-phasic particles fabricated in accordance with certain methods of the present disclosure. FIGS. 11A-11F show SEM images of bi-phasic amphiphilic particles comprising polymer layers of SU-8 (dyed red and shown as the lower layer) and PEGDA (dyed blue and shown as the upper layer) released from a template having a hexagonal shape (FIG. 11A), a square shape (FIG. 11B), a complex "M" shape (FIG. 11C), and circular shapes (FIGS. 11D, 11E and 11F). FIG. 11G shows triphasic particles comprising SU-8-PEGDA-SU-8 layers or phases. FIG. 11H shows organic-inorganic, hybrid multiphasic particles composed of SU-8 and SiO$_2$ nanoparticle layers, including a detailed image of a particle in the top inset. FIG. 11I shows biphasic polymeric nanoparticles comprising SU-8-PS layers having a diameter of about 25 nm. The top insets in FIGS. 11A-11C and 11G show corresponding 3-D stacked fluorescence confocal microscopy images of the particles before release and removal from the template. SU-8 is dyed red and forms the lower layer, while PEGDA is dyed blue and forms the upper layer. Scale bars for the top insets in FIGS. 11A-11C and 11G represent 100 μm. The top insets in FIGS. 11D-11F show cross-sectional SEM images of the layers within the particles before release and removal from the template, where PSS is a sacrificial layer formed over the template. The bottom insets in FIGS. 11A-11B, and 11G-11H show the corresponding AFM height images and thickness (t) of the released particles.

Figure 12A:
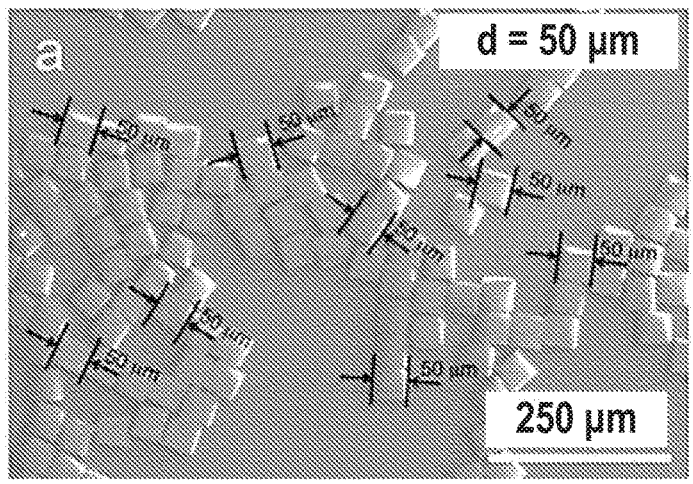
Figure 12B:
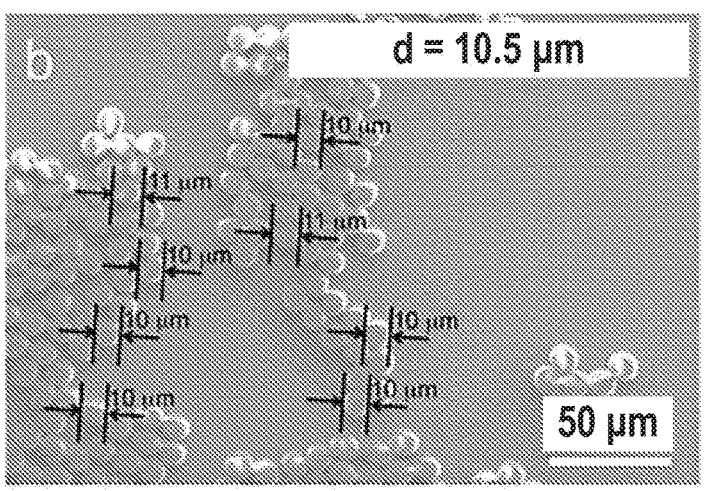
Figure 12C:
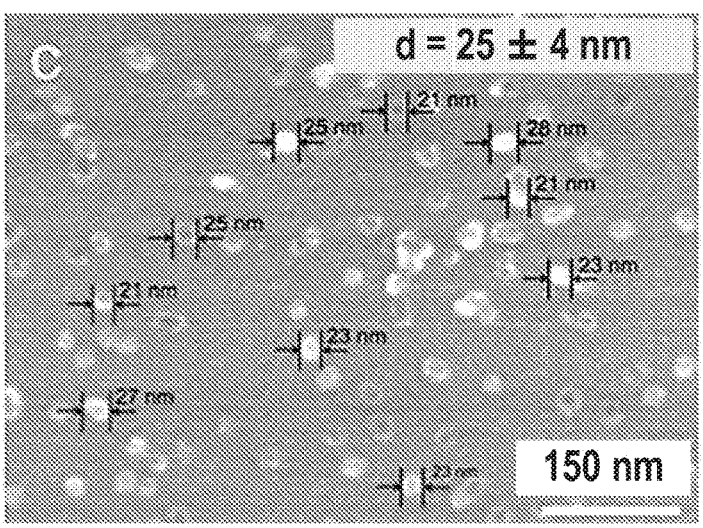

FIGS. 12A-12C show SEM images of various bi-phasic, micro- and nano-particles removed from a template after being formed in methods in accordance with certain aspects of the present disclosure showing monodispersity of such biphasic particles. FIG. 12A shows monodisperse square-shaped PEGDA-SU-8 multiphasic particles having an average diameter of about 50 μm. FIG. 12B shows monodisperse circular-shaped PEGDA-SU-8 multiphasic particles having an average diameter of about 10 µm. FIG. 12C shows monodisperse circular-shaped PEGDA-SU-8 multiphasic particles having an average diameter of about 25 nm. The average value for the particle dimensions "d" shown in the images is an average over at least 100 particles.

Figures 13I, 13J:
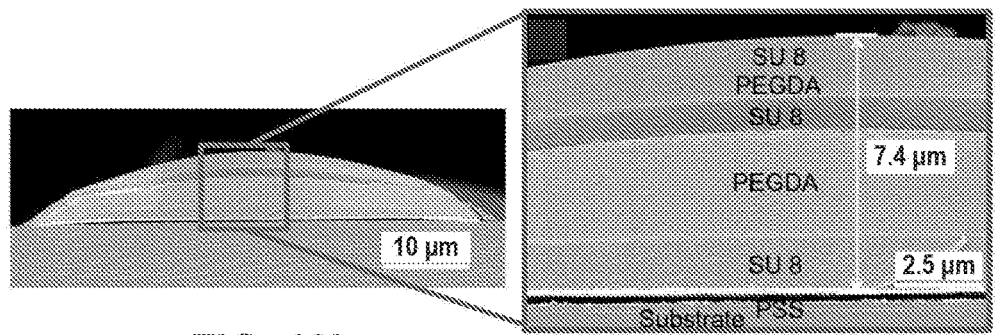
Figures 13K, 13L:
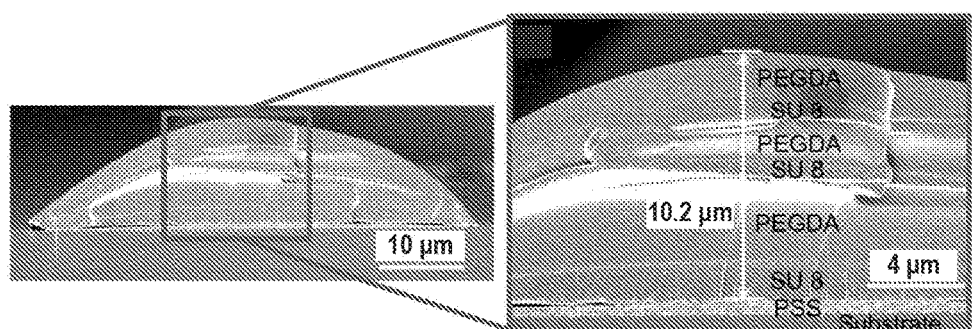
Figure 13M:
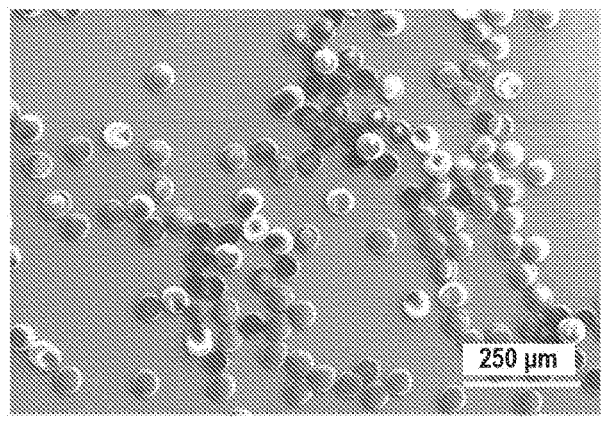

FIGS. 13A-13M show different stages of the fabrication process according to certain aspects of the present disclosure used to form hexa-phasic particles. FIGS. 13A, 13C, 13E, 13G, 13I, and 13K are SEM images showing cross sections after sequential polymer depositions of SU-8 and PEGDA within a single wettable circular-shaped region (50 µm in diameter). FIGS. 13B, 13D, 13F, 13H, 13J, and 13L show high magnification images of the area indicated by the square shown in FIGS. 13A, 13C, 13E, 13G, 13I, and 13K, respectively. FIG. 13M shows released hexa-phasic particles upon the dissolution of the sacrificial PSS layer.

FIGS. 14A-14D show tri-phasic particles formed in accordance with certain aspects of the present disclosure that are integrated with three different functionalities. FIG. 14A shows a cross-sectional SEM image of a tri-functional tri-phasic particle comprising a first phase having SU-8 loaded with magnetite nano-particles, a second phase having SU-8 loaded with a fluorescent red dye, and a third phase that is a hydrogel (cross-linked PEGDA). FIG. 14B shows a higher magnification image of the area indicated by the square shown in FIG. 14A. FIG. 14C shows a fluorescent microscope image of the tri-functional particles after removal from a template surface. FIG. 14D shows motion of a cluster of tri-functional particles on a water surface by using an external magnetic field applied in different directions. The inset shows a detailed view of the trifunctional particles.

Figure 15A:
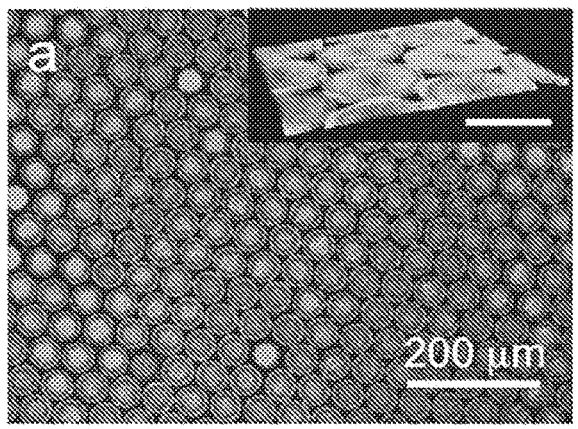
Figure 15B:
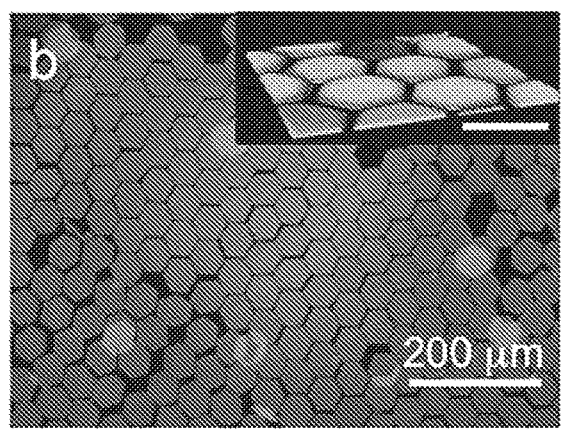
Figure 15C:
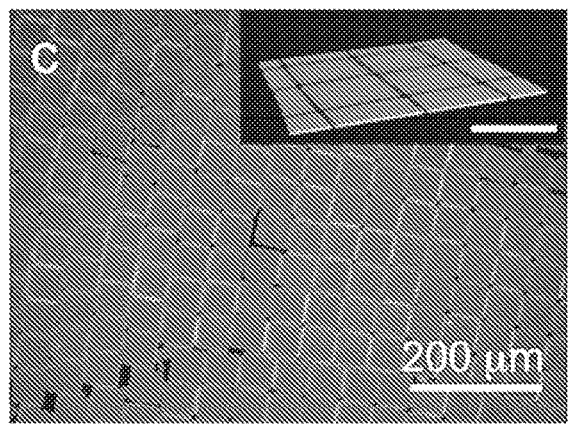

FIGS. 15A-15C show two-dimensional self-assembly of fabricated bi-phasic amphiphilic particles formed in accordance with certain aspects of the present disclosure at an oil-water interface. FIG. 15A shows self-assembled, close packed structures at an oil (top)—water (bottom) interface formed by circular-shaped particles. FIG. 15B shows self-assembled close packed structures having hexagon-shaped particles, while FIG. 15C shows square-shaped, bi-phasic amphiphilic particles self-assembled. The top insets show corresponding 3-D stacked fluorescence confocal microscopy images of the respective assemblies. Scale bars in the insets represent 50 µm.

Figure 16A:
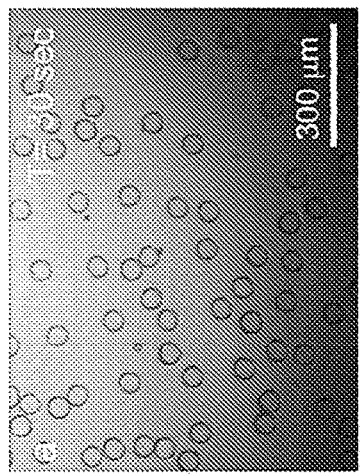
Figure 16B:
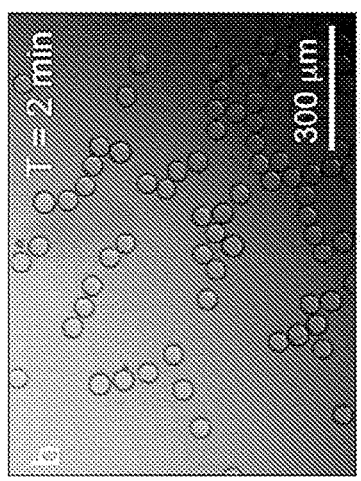
Figure 16C:
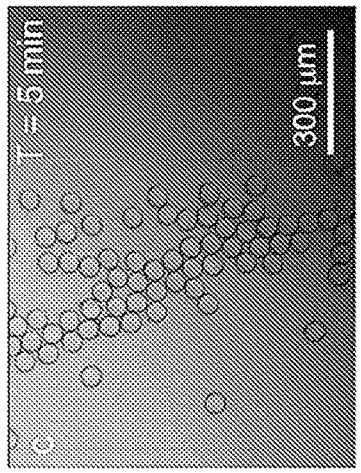
Figure 16D:
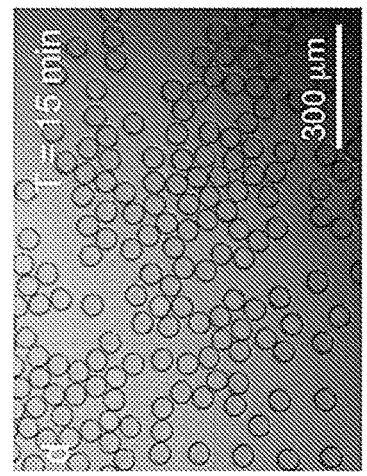
Figure 16E:
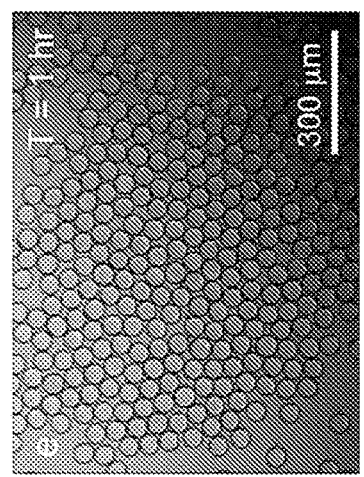
Figure 16F:
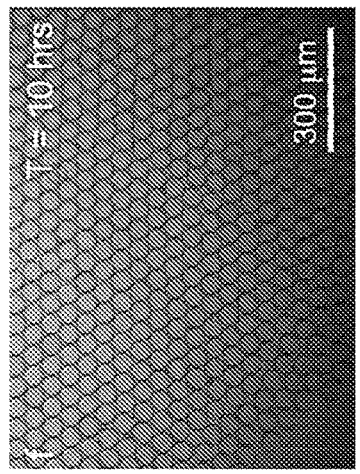

FIGS. 16A-16F show time lapsed optical microscopy images of a self-assembly process for biphasic polymer particles formed in accordance with the present disclosure at an oil-water interface over a period of 10 hours. FIG. 16A is taken at 30 seconds, FIG. 16B at 2 minutes, FIG. 16C at 5 minutes, FIG. 16D at 15 minutes, FIG. 16E at 1 hour, and FIG. 16F at 10 hours.

Figures 17A, 17B, 17C:
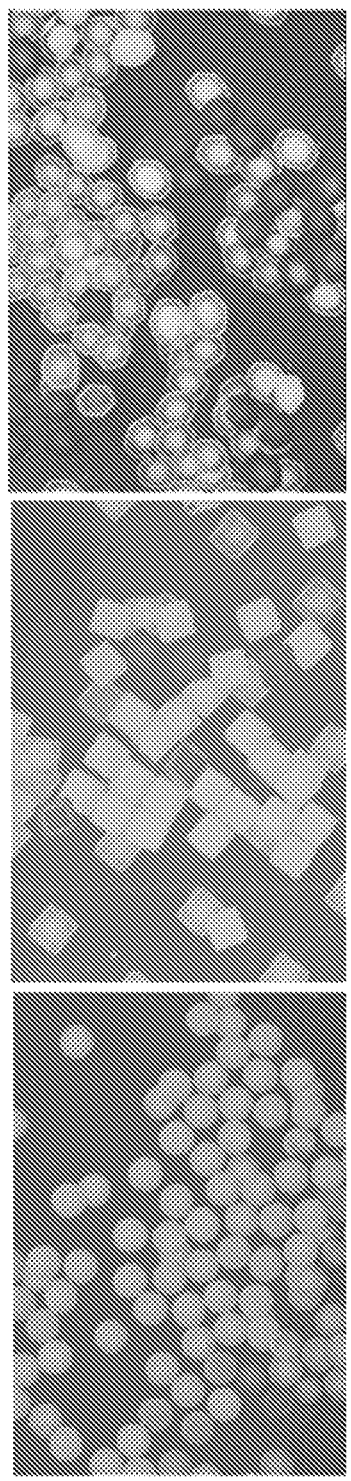

FIGS. 17A-17C show SEM images of different biphasic particles formed in accordance with certain aspects of the present disclosure comprising layered PSS/PAH polyelectrolytes having circular (FIG. 17A), square (FIG. 17B), and hexagonal cross-sectional (FIG. 17C) shapes.

Corresponding reference numerals indicate corresponding parts throughout the several views of the drawings.

DETAILED DESCRIPTION

Example embodiments will now be described more fully with reference to the accompanying drawings.

Example embodiments are provided so that this disclosure will be thorough, and will fully convey the scope to those who are skilled in the art. Numerous specific details are set forth such as examples of specific compositions, components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed, unless otherwise indicated.

When a component, element, or layer is referred to as being "on," "engaged to," "connected to," or "coupled to" another element or layer, it may be directly on, engaged, connected or coupled to the other component, element, or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various steps, elements, components, regions, layers and/or sections, these steps, elements, components, regions, layers and/or sections should not be limited by these terms, unless otherwise indicated. These terms may be only used to distinguish one step, element, component, region, layer or section from another step, element, component, region, layer or section. Terms such as "first," "second," and other numerical terms when used herein do not imply a sequence or order unless clearly indicated by the context. Thus, a first step, element, component, region, layer or section discussed below could be termed a second step, element, component, region, layer or section without departing from the teachings of the example embodiments.

Spatially or temporally relative terms, such as "before," "after," "inner," "outer," "beneath," "below," "lower," "above," "upper," and the like, may be used herein for ease of description to describe one element or feature's relationship to another element(s) or feature(s) as illustrated in the figures. Spatially or temporally relative terms may be intended to encompass different orientations of the device or system in use or operation in addition to the orientation depicted in the figures.

It should be understood for any recitation of a method, composition, device, or system that "comprises" certain steps, ingredients, or features, that in certain alternative variations, it is also contemplated that such a method, composition, device, or system may also "consist essentially of" the enumerated steps, ingredients, or features, so that any other steps, ingredients, or features that would materially alter the basic and novel characteristics of the invention are excluded therefrom.

Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters.

In addition, disclosure of ranges includes disclosure of all values and further divided ranges within the entire range, including endpoints and sub-ranges given for the ranges.

In various aspects, the present disclosure provides a facile technique for fabricating a comprehensive library of multiphasic particles, which may be termed Wettability Engendered Templated Self-assembly (WETS). Thus, in certain aspects, methods of forming multiphasic particles, such as multiphasic microparticles or nanoparticles, employ a template that defines a first region that is wettable to a wide variety of liquid substances, including polar and non-polar liquids, like water and oils. The template also defines a second region that is non-wettable to a wide variety of liquid substances, including polar and non-polar liquids.

Thus, a method according to the present disclosure creates a multiphasic particle. In certain aspects, the method may first create a release layer on a surface of the template. A first liquid composition may thus be applied to the surface of the template defining the first and second regions, one of which is wettable and the other of which is non-wettable to polar and non-polar liquids. The first liquid composition remains in the first region, but is repelled by the second region. In this manner, a release layer that is a solid or semi-solid is formed within the first region of the template. Then, a second liquid composition is applied over the release layer. The second liquid may comprise one or more polymers or polymer precursors (e.g., a polymer solution) and/or a dispersion of one or more particles. The second liquid composition remains in the first region and forms a first layer that is a solid or semi-solid. Next, a third liquid composition is applied over the first layer. The third liquid composition similarly remains in the first region and forms a second layer that is a solid or semi-solid over the first layer. The second and third liquid compositions, and thus the first and second layers, are compositionally distinct from one another. By compositionally distinct, it is meant that the layers differ in chemical composition from one another by at least one ingredient or component. In certain variations, compositionally distinct layers may not share any common ingredients or components. After the deposition of layers is completed, the first layer and the second layer may then be released from the template by removing the release layer (e.g., by dissolving or disintegrating the release layer) to create a multiphasic particle comprising at least the first layer and the second layer. Such multiphasic particles have precisely controlled shapes facilitated by highly defined boundaries between the first and second regions of the template.

The synthesis methodology according to certain aspects of the present disclosure may include fabricating a template having a non-wettable surface (e.g., omniphobic and thus non-wettable to both polar and non-polar liquids) patterned with monodisperse, wettable domains (e.g., omniphilic to polar and non-polar liquids). The wettable domains may be preselected to have different sizes and shapes. Liquids that optionally comprise polymer solutions or particle dispersions are applied to the patterned template (e.g., by dip-coating). The polymer(s) and/or the particle(s) preferentially self-assemble within the wettable domains or regions. The carrier in the liquid may then be removed (e.g., by volatilization or evaporation) to form a semi-solid or solid material layer. Utilizing this phenomenon, multiphasic particles may be fabricated with precisely controlled geometry and compositions through multiple, layered, deposition steps of distinct liquid compositions (containing different polymers and/or particles) within the patterned domains. In this manner, multiple distinct layers or phases may be formed to create a multiphasic particle. Furthermore, the layers or phases may be anisotropic within the multiphasic particle.

Upon releasing these multiphasic assemblies from the template by removing the sacrificial release layer, multiphasic particles may be obtained. In this manner, the inventive WETS techniques provide an unprecedented ability to manufacture monodisperse, multiphasic particles possessing almost any desired shape, composition, modulus, or dimension (e.g., having dimensions as small as 10 nm), using a simple dip-coating or other straightforward application process. Such multiphasic particles have precisely controlled and potentially complex geometries.

In various aspects, the present disclosure provides multiphasic particles that have a plurality of physically and/or compositionally distinct phases, such as shown in FIGS. 1 and 2. By the term "phase" it is meant that a portion of a particle is chemically and/or physically distinct from another portion of the component. The phase may be a layer of material in certain variations. The multiphasic particles according to the present disclosure include a first phase and at least one phase that is distinct from the first phase.

In certain configurations, such as that shown in FIG. 1, a multiphasic particle 20 has a first layer 22 that defines a first phase. Each respective phase occupies a spatially discrete region or compartment of the particle 20. A second layer 24 defines a second phase. Thus, the first layer 22 is stacked on the second layer 24, so that the first layer 22 defines a first major lateral dimension 30 (e.g., a major horizontal plane defined by a plane corresponding to the surface defined by the circumference of the particle as shown in FIG. 1) and the second layer 24 defines a second major lateral dimension 32. The multiphasic particle 20 also defines a major longitudinal dimension 34 (e.g., length). The first major lateral dimension 30 and the second major lateral dimension 32 are perpendicular to a major longitudinal dimension 34 of the multiphasic particle 20. Multiphasic particles formed in accordance with the present disclosure may have a variety of shapes or morphologies and are not limited to the cylindrically shaped particle shown in FIG. 1.

In various aspects, the multiphasic particle may be a "microparticle" having at least one spatial dimension on a micro-scale that is less than about 100 μm (i.e., 100,000 nm), optionally less than about 50 μm (i.e., 50,000 nm), optionally less than about 10 μm (i.e., 10,000 nm), optionally less than or equal to about 5 µm (i.e., 5,000 nm), and in certain aspects less than or equal to about 1 µm (i.e., 1,000 nm). "Nano-sized" particles are generally understood by those of skill in the art to have at least one spatial dimension that is less than about 50 µm (i.e., 50,000 nm), optionally less than about 10 µm (i.e., 10,000 nm), optionally less than about 1 µm (i.e., less than about 1,000 nm).

In various aspects, the dimensions of the multiphasic particle are of a relatively small scale, for example, on a microscale. A "microparticle" as used herein encompasses "nanoparticle." It should be noted that so long as at least one dimension of the particle falls within the above-described micro-sized scale (for example, diameter), one or more other axes may well exceed the micro-size (for example, length). However, in preferred aspects, all of the dimensions of the particle fall within the micro-sized scale. A "nano-particle" generally refers to a particle where all three spatial dimensions are nano-sized and less than or equal to several micrometers (e.g., less than about 50 µm or 50,000 nm).

Thus, in certain aspects, depending upon the application, a microparticle may have a major longitudinal dimension or axis 34, such as length, that is less than or equal to about 500 µm, optionally less than or equal to about 400 µm, optionally less than or equal to about 300 µm, optionally less than or equal to about 200 µm, optionally less than or equal to about 100 µm, optionally less than or equal to about 75 µm, optionally less than or equal to about 50 µm, optionally less than or equal to about 25 µm, optionally less than or equal to about 10 µm, optionally less than or equal to about 5 µm, optionally less than or equal to about 3 µm, optionally less than or equal to about 2 µm, optionally less than or equal to about 1 µm, optionally less than or equal to about 900 nm, optionally less than or equal to about 800 nm, optionally less than or equal to about 700 nm, optionally less than or equal to about 600 nm, optionally less than or equal to about 500 nm, optionally less than or equal to about 400 nm, optionally less than or equal to about 300 nm, optionally less than or equal to about 200 nm, optionally less than or equal to about 100 nm, optionally less than or equal to about 90 nm, optionally less than or equal to about 80 nm, optionally less than or equal to about 70 nm, optionally less than or equal to about 60 nm, optionally less than or equal to about 50 nm, optionally less than or equal to about 40 nm, optionally less than or equal to about 30 nm, optionally less than or equal to about 25 nm, optionally less than or equal to about 20 nm, optionally less than or equal to about 15 nm, and in certain aspects, equal to about 10 nm.

Further, multiphasic particles formed in accordance with certain aspects of the present disclosure, are particles. Generally, an aspect ratio (AR) for particles, including cylindrical shapes (e.g., a pillar, a rod, tube, etc.) is defined as AR=L/D, where L is the length of the longest axis (here the major longitudinal axis 34) and D is the diameter of the particle (e.g., the diameter along the first major lateral dimension 30/second major lateral dimension or axis 32). Suitable particles formed in accordance with certain aspects of the present disclosure may have aspect ratios of less than or equal to about 100, optionally less than or equal to about 75, optionally less than or equal to about 50, optionally less than or equal to about 25, optionally less than or equal to about 10, optionally less than or equal to about 5, optionally less than or equal to about 1, optionally less than or equal to about 0.5, optionally less than or equal to about 0.1, optionally less than or equal to about 0.05, optionally less than or equal to about 0.01, optionally less than or equal to about 0.005, and in certain aspects, optionally less than or equal to about 0.001, by way of example. In certain variations, an aspect ratio of a particle formed in accordance with the present teachings may be less than or equal to about 1. In certain variations, an aspect ratio of a particle is greater than or equal to about 0.01 to less than or equal to about 0.2.

In certain aspects, each respective phase of the multiphasic particle is exposed to an external environment, thus providing exposure of the respective phase surfaces of the multiphasic particle to an external environment. The exposure of each respective surface of each phase provides enhanced environmental interface and optimum diffusion or material transfer, resulting increased availability. For example, the multiphasic particle 20 shown in FIG. 1 has three phase interfaces. In FIG. 1, a multiphasic particle 20 has a first phase interface 40 between first layer 22 and second layer 24, where both the first phase of first layer 22 and second phase of second layer 24 occupy discrete spatial locations within the particle 20. First layer 22 also interacts with an external environment 50 at a second phase interface 42 that extends along the circumference of the layer and the upper surface. Lastly, the second layer 24 has a third phase interface 44 with the medium 50 that extends along the circumference of the layer and the bottom surface. In certain variations, the first layer 22 thus extends laterally across the multiphasic microparticle 20 and is exposed along peripheral external surfaces (corresponding to first phase interface 40), while the second layer 24 likewise extends laterally across and is exposed along the peripheral external surfaces (corresponding to first phase interface 44) of the multiphasic microparticle 20.

In certain aspects, the multiphasic particles of the present disclosure include multiple distinct phases, for example three distinct phases, as shown in FIG. 2 as multiphasic particle 60. While not shown here, three or more phases are contemplated by the present teachings as well. Multiphasic particle 60 has four phase interfaces. The multiphasic particle 60 has a first layer 62 that defines a first phase. A second layer 64 defines a second phase. A third layer 66 defines a third phase. Thus, the first layer 62 is stacked on the second layer 64, which is itself stacked on the third layer 66, so that the first layer 62 defines a first major lateral dimension 70 (e.g., a major horizontal plane defined by the circumference of the particle as shown in FIG. 2), the second layer 64 defines a second major lateral dimension 72, and the third layer 66 defines a third major lateral dimension 74. The first major lateral dimension 70, second major lateral dimension 72, and third major lateral dimension 74 are parallel to one another. The multiphasic particle 60 also defines a major longitudinal dimension 76. The first major lateral dimension 70, the second major lateral dimension 72, and the third major lateral dimension 74 are all perpendicular to the major longitudinal dimension 76 of the multiphasic particle 60.

A first phase interface 80 occurs between first layer 62 and second layer 64, where both the first phase of first layer 62 and second phase of second layer 64 occupy discrete spatial locations within the particle 60. First layer 62 also interacts with an external environment 90 at a second phase interface 82 that extends along the circumference of the layer and the upper surface. The second layer 64 has a third phase interface 84 with the external environment 90 that extends around the circumference of the layer and a third phase interface 86 with the third layer 66. Third layer 66 also defines a fourth phase interface 88 with the external environment 90 that extends along the circumference of the layer and the bottom surface.

In certain aspects, the multiphasic particles comprise materials in a solid phase or a semi-solid phase. As mentioned above, the multiphasic particles may have a variety of geometries or morphologies including, by way of non-limiting example, spheres, rods/cylinders, prisms of rectangles, triangles, or polygons, pyramids, disks, toroids, cones, and the like. The shape of the multiphasic particle formed relates to the predetermined shape that defines the first wettable region on the surface of the template.

As shown in FIG. 3, a template 92 has a surface 94 of a substrate 96. The substrate 96 may be made of variety of materials, such as titanium oxide ($TiO_2$), zinc oxide (ZnO), tin oxide ($SnO_2$), tungsten oxide ($WO_3$), vanadium oxide ($V_2O_5$), and combinations thereof. The surface 94 defines one or more first regions 98 that are wettable and form a pattern in a second region 100 that is non-wettable. In certain variations, the first region(s) 98 have a first receding contact angle of less than or equal to about 5° for both non-polar and polar liquids making the first region wettable to a wide variety of substances, including polar (e.g., water) and non-polar (e.g., oil) liquids. The second region(s) 100 have a second receding contact angle of greater than or equal to about 10° for both non-polar and polar liquids, making the second region(s) 100 non-wettable to a variety of substances including water-containing and oil-containing liquids. In certain variations, the first and second regions 98, 100 may exhibit extreme wettabilities.

Surfaces possessing extreme wettabilities are generally understood to be those that display extreme wetting (e.g., contact angles nearing 0°) or non-wetting (e.g., contact angles of greater than or equal to about 120°) with different liquids. In general, liquids may be classified as polar (such as water, alcohols, dimethyl formamide and the like) and non-polar (such as various oils). Notably, the use of "hydro" nomenclature is intended to encompass both water and polar liquids, while "oleo" nomenclature encompasses non-polar liquids, including oils. Extreme wettabilities may therefore include a surface that is both superhydrophobic and superoleophobic or alternatively, both superhydrophilic and superoleophilic.

By way of further background, extreme wettability can be understood in the context of the following. The primary measure of wetting of a liquid on a non-textured (or smooth) surface is the equilibrium contact angle θ, given by Young's relation as:

$$\cos\theta = \frac{\gamma_{SV} - \gamma_{SL}}{\gamma_{LV}}. \quad \text{(Equation 1)}$$

γ refers to the interfacial tension, and S, L, and V designate the solid, liquid, and vapor phases, respectively. The solid-vapor interfacial tension ($\gamma_{SV}$) and the liquid-vapor interfacial tension ($\gamma_{LV}$) are also commonly referred to as the solid surface energy and the liquid surface tension, respectively. When a liquid comes in contact with a smooth homogenous surface, it can either wet the surface completely, or partially, making a finite equilibrium contact angle ($\theta_E$) with the surface. The equilibrium contact angle is determined by the balance between the solid-vapor ($\gamma_{SV}$ or the surface energy), solid-liquid ($\gamma_{SL}$) and liquid-vapor ($\gamma_{LV}$ or the surface tension) interfacial tensions acting at the three-phase contact line.

Non-textured surfaces that display contact angles θ greater than or equal to about 90° with water (or other polar liquids) are considered to be hydrophobic and surfaces that display contact angles greater than or equal to about 90° with oil (or other non-polar liquids) are considered to be oleophobic. Typically, surfaces with high $\gamma_{SV}$ tend to be hydrophilic, whereas those with low $\gamma_{SV}$ (such as highly fluorinated compounds) tend to be hydrophobic.

Surfaces that spontaneously approach a contact angle θ of 0° with water and oil are generally considered superhydrophilic and superoleophilic respectively and surfaces the approach contact angles θ greater than or equal to about 150° and low contact angle hysteresis (difference between the advancing $\theta_{adv}$ and the receding contact angle $\theta_{rec}$) with water and oil are generally considered to be superhydrophobic and superoleophobic, respectively. In certain variations, the first and second regions of a template (e.g., first regions 98 and second regions 100 of template 92 in FIG. 3) for forming multiphasic particles may exhibit extreme wettabilities.

Surfaces that display a contact angle θ of less than or equal to about 90°, optionally of less than or equal to about 85°, optionally of less than or equal to about 80°, optionally of less than or equal to about 75°, optionally of less than or equal to about 70°, optionally of less than or equal to about 65°, optionally of less than or equal to about 60°, optionally of less than or equal to about 55°, optionally of less than or equal to about 50°, and in certain aspects, optionally of less than or equal to about 45° with water or other polar liquids (e.g., alcohols, dimethyl formamide and the like) are considered to be "hydrophilic."

As used herein, surfaces that display a contact angle θ of less than or equal to about 5°, optionally of less than or equal to about 4°, optionally of less than or equal to about 3°, optionally of less than or equal to about 2°, optionally of less than or equal to about 1°, and in certain aspects, 0° with water or other polar liquids (e.g., alcohols, dimethyl formamide and the like) are considered to be "superhydrophilic."

Surfaces that display a contact angle of greater than or equal to about 90°, optionally greater than or equal to about 95°, optionally greater than or equal to about 100°, optionally greater than or equal to about 105°, optionally greater than or equal to about 110°, optionally greater than or equal to about 115°, optionally greater than or equal to about 120°, optionally greater than or equal to about 125°, optionally greater than or equal to about 130°, optionally greater than or equal to about 135°, optionally greater than or equal to about 140°, and in certain aspects, optionally greater than or equal to about 145° with water or other polar liquids are considered to be "hydrophobic."

Superhydrophobic surfaces are those that display a contact angle of greater than or equal to about 150°, optionally greater than or equal to about 151°, optionally greater than or equal to about 152°, optionally greater than or equal to about 153°, optionally greater than or equal to about 154°, optionally greater than or equal to about 155°, optionally greater than or equal to about 156°, optionally greater than or equal to about 157°, optionally greater than or equal to about 158°, optionally greater than or equal to about 159°, and in certain aspects, optionally greater than or equal to about 160° along with low contact angle hysteresis (difference between the advancing $\theta_{adv}$ and the receding contact angle $\theta_{rec}$) with water or other preselected polar liquids. In certain variations, a "superhydrophobic" surface has a contact angle of greater than or equal to about 150° and less than or equal to about 180° with water or another polar liquid.

Surfaces that display a contact angle θ of less than or equal to about 90°, optionally of less than or equal to about 85°, optionally of less than or equal to about 80°, optionally of less than or equal to about 75°, optionally of less than or equal to about 70°, optionally of less than or equal to about 65°, optionally of less than or equal to about 60°, optionally of less than or equal to about 55°, optionally of less than or equal to about 50°, and in certain aspects, 45° with oil (a preselected reference oil or other non-polar liquid) are considered to be "oleophilic." A "preselected oil" is intended to include any oil or combinations of oils of interest.

Likewise, surfaces that display a contact angle θ of less than or equal to about 5°, optionally of less than or equal to about 4°, optionally of less than or equal to about 3°, optionally of less than or equal to about 2°, optionally of less than or equal to about 1°, and in certain aspects, 0° with oil (a preselected reference oil or other non-polar liquid) are considered to be "superoleophilic."

Surfaces that display a contact angle of greater than or equal to about 90°, optionally greater than or equal to about 95°, optionally greater than or equal to about 100°, optionally greater than or equal to about 105°, optionally greater than or equal to about 110°, optionally greater than or equal to about 115°, optionally greater than or equal to about 120°, optionally greater than or equal to about 125°, optionally greater than or equal to about 130°, optionally greater than or equal to about 135°, optionally greater than or equal to about 140°, and in certain aspects, optionally greater than or equal to about 145° with a preselected oil are considered to be "oleophobic." Due to the low surface tension values for oils, in spite of numerous known natural superhydrophobic surfaces, there are no known, naturally-occurring, superoleophobic surfaces.

Superoleophobic surfaces are those that display a contact angle of greater than or equal to about 150°, optionally greater than or equal to about 151°, optionally greater than or equal to about 152°, optionally greater than or equal to about 153°, optionally greater than or equal to about 154°, optionally greater than or equal to about 155°, optionally greater than or equal to about 156°, optionally greater than or equal to about 157°, optionally greater than or equal to about 158°, optionally greater than or equal to about 159°, and in certain aspects, optionally greater than or equal to about 160° along with low contact angle hysteresis (difference between the advancing $\theta_{adv}$ and the receding contact angle $\theta_{rec}$) with preselected low surface tension liquids, such as a representative oil (for example, rapeseed oil (RSO)). In certain variations a "superoleophobic" surface has a contact angle of greater than or equal to about 150° and less than or equal to about 180° with a preselected oil, like representative RSO oil.

Oleophobic and superoleophobic surfaces are generally hydrophobic and/or superhydrophobic, because the surface tension of water is significantly higher than that of oils. In certain aspects, the present teachings contemplate omniphobic surfaces that are surfaces that repel (or are non-wetting to) almost all known liquids, polar or non-polar. Thus, omniphobic surfaces can be considered to be both hydrophobic and oleophobic, while superomniphobic can be considered to be both superhydrophobic and superoleophobic, as discussed previously. Omniphobic surfaces are generally indicated to have contact angles $\theta_{OIL}$ and $\theta_{H2O}$ of greater than 90°. Omniphobic surfaces may have an oil contact angle $\theta_{OIL}$ of greater than or equal to about 90° to less than or equal to about 180° and a water contact angle $\theta_{H2O}$ of greater than or equal to about 90° to less than or equal to about 180°. While omniphobic wettability encompasses superomniphobic wettability, superomniphobic surfaces are typically considered to have $\theta_{OIL}$ and $\theta_{H2O}$ of greater than or equal to about 150° up to about 180°, by way of example and as discussed previously above.

Figure 4:
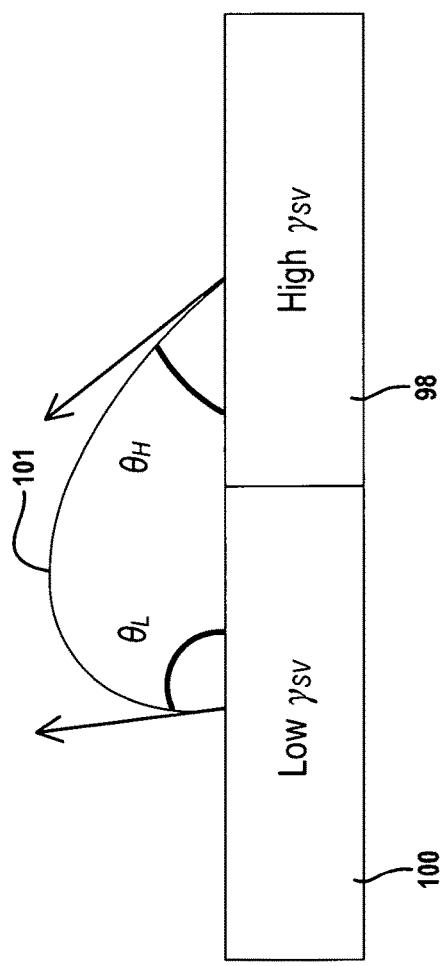
FIG. 4 shows a cross-section of a template having a liquid droplet disposed thereon, where the liquid droplet is in contact with both wettable and non-wettable regions of the template, like that shown in FIG. 3.

FIG. 4 illustrates the driving factors present for the wettability engendered assembly of liquids within patterned wettable domains on a non-wettable surface according to the present teachings. FIG. 4 shows a cross-section of a liquid droplet 101 in contact with both a wettable first region 98 and a non-wettable second region 100 (showing a cross-sectional view of the boundary between a first region 98 and a second region 100 in FIG. 3). As shown, the surface of the wettable first region 98 has a relatively high surface energy ("High $\gamma_{SV}$"), while the non-wettable second region 100 has a relatively low surface energy ("Low $\gamma_{SV}$"). The liquid contact angle on the wettable first region is designated $\theta_H$, while the liquid contact angle on the non-wettable second region is designated $\theta_L$.

When a liquid droplet 101 comes into contact with a non-wettable surface 100 (possessing low surface energy Low $\gamma_{SV}$) patterned with wettable domains 98 (possessing high surface energy—High $\gamma_{SV}$), the droplet 101 wets and preferentially assembles within the wettable domains 98. This wettability engendered self-assembly of the liquid 101 within the patterned wettable domains 98 is due to the unbalanced forces acting on the droplet edge (solid-liquid-air three phase contact line).

The unbalanced force (dFS) experienced by a section of the droplet with thickness dx is given by:

$$dF_S = \gamma_{LV}(\cos\theta_H - \cos\theta_L)dx \quad (1)$$

Here, $\gamma_{LV}$ is the surface tension of the liquid, and $\theta_H$ and $\theta_L$ are the Young's contact angles of the liquid in the high and low surface energy regions, respectively (as in FIG. 4). The total force ($F_S$) on the droplet 101 can be obtained by integrating equation (1) over the entire width of the droplet. This force drives the droplet towards the surface with higher solid surface energy because $\theta_H < \theta_L$.

However, for surfaces that display high contact angle hysteresis—CAH (the difference between the contact angles as a liquid droplet advances or recedes from a surface), the receding contact angle on the non-wettable surface (100) may be smaller than the advancing contact angle on the wettable domains (98). In such cases, the liquid droplet 101 will not advance into the wettable domains 98. Thus, a non-wettable surface possessing a low contact angle hysteresis, when patterned with wettable domains, can act as a template to engender the self-assembly of liquids within the patterned wettable domains.

Another important parameter to consider while applying a liquid to a patterned surface (e.g., via dip coating) is that there is a maximum dip-coating velocity (critical velocity $V_C$) above which a liquid will not dewet off a surface, even if the surface exhibits a finite receding contact angle. This critical velocity depends on the viscosity ($\eta$) and surface tension ($\gamma_{LV}$) of the liquid, and is given by:

$$V_C = k\frac{\gamma_{LV}}{\eta}\theta_E^3 \quad (2)$$

Here, k is proportionality constant. Below this critical dip-coating velocity, the liquid dewets off a non-wettable or partially wettable surface completely. The non-wettable surfaces developed in accordance with the present disclosure have high receding contact angles ($\theta_R > 20°$; see also Table 1 below) for almost all liquids (including fluorinated solvents). This leads to relatively high critical dip coating velocities, typically in the range of greater than or equal to about 0.1 cm/sec to less than or equal to about 1 cm/sec.

The contact angles for a liquid as it advances or recedes from a smooth surface are called the advancing ($\theta_A$) and receding ($\theta_R$) contact angles, respectively. When a substrate with a receding contact angle, $\theta_R = 0$ is pulled through a liquid, the substrate is coated with a uniform liquid film of finite thickness, controlled by the dip-coating velocity. In contrast, when a partially wetting surface ($\theta_R$>0) is dip-coated, the liquid film is unstable and dewets off the surface, leaving the surface completely dry when dip-coating velocities are below a critical value. Similarly, when a non-wettable (or low surface energy) surface patterned with wettable domains is dip-coated (for example, on a surface of a template prepared in accordance with certain aspects of the present disclosure), the liquid wets and coats only the wettable (or high surface energy) domains and leaves the non-wettable surface completely dry. This wettability engendered self-assembly of the liquid within the patterned wettable domains is due to unbalanced forces acting on the solid-liquid-air three phase contact line.

Conventionally, there were numerous difficulties to self-assemble low surface tension organic liquids (such as alcohols, dimethyl formamide, tetrahydrofuran, toluene, and the like) or polymer solutions within patterned high surface energy domains. This is because organic solvents and polymer solutions possess low surface tension values ($\gamma_{LV}$~15-30 mN/m), and as a consequence they tend to wet and spread on both the high and low surface energy patterned domains, forming a film over the entire surface. However, in accordance with principles of the present disclosure, a patterned surface of a template, prepared as discussed further below, defines one or more regions that have a material that is non-wettable to polar and non-polar liquids, despite having low surface tensions. The polar or non-polar liquids wet the wettable surface regions, while concurrently being repelled from the non-wettable surface regions that remain dry, unlike in conventional technologies.

Therefore, in certain variations, a second region of a surface of template that is non-wettable may be omniphobic or superomniphobic and may have a receding contact angle of greater than or equal to about 10° for both non-polar and polar liquids, optionally greater than or equal to about 15°, optionally greater than or equal to about 20°, reflecting non-wetting behavior to a variety of polar and non-polar substances applied thereto.

Omniphilic surfaces have an oil contact angle $\theta_{OIL}$ of greater than or equal to about 0° to less than or equal to about 90° and a water contact angle $\theta_{H2O}$ of greater than or equal to about 0° to less than or equal to about 90°. Omniphilic surfaces are those surfaces that are wet by all liquids, polar or non-polar. Omniphilic surfaces generally are indicated to have contact angles $\theta_{OIL}$ and $\theta_{H2O}$ of less than 90°, while superomniphilic surfaces may have $\theta_{OIL}$ and $\theta_{H2O}$ of greater than 0 up to about 30°, by way of example.

Therefore, in certain variations, a first region of the surface of the template is wettable may be omniphilic or superomniphilic and may have a receding contact angle of less than or equal to about 5° for both non-polar and polar liquids, optionally less than or equal to about 4°, optionally less than or equal to about 3°, optionally less than or equal to about 2°, and in certain variations, optionally less than or equal to about 1°, and in certain more preferred variations, about 0°, reflecting a surface region that is fully wettable to a variety of polar and non-polar substances applied thereto.

Figure 5:
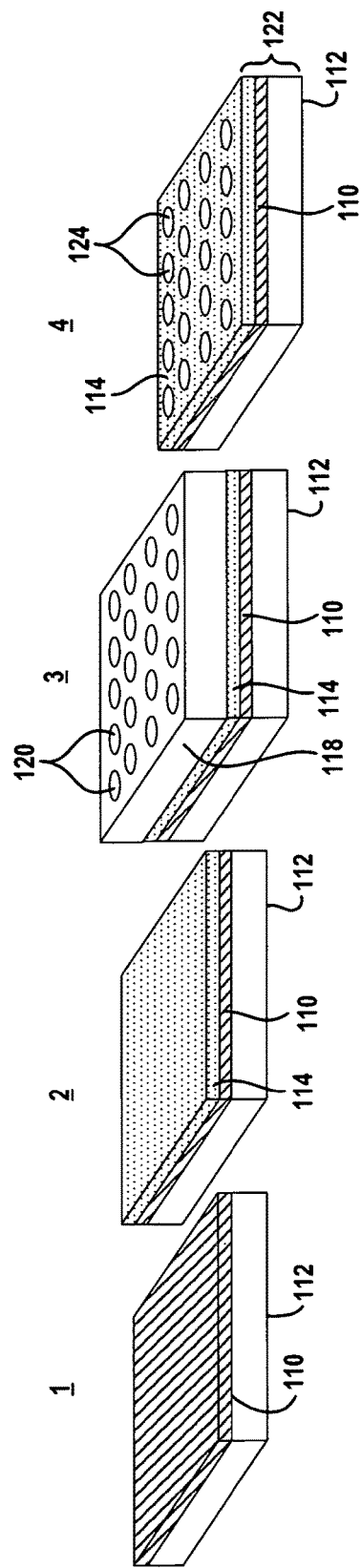
FIG. 5 shows a schematic of a process of making a template for forming multiphasic particles in accordance with certain aspects of the present disclosure.

In certain aspects, the disclosure thus provides methods of forming such templates for conducting a WETS process to form a multiphasic microparticle. In one variation of a process illustrated in FIG. 5, a template may be formed by applying a metal oxide material 110 to a substrate 112, as shown at 1. The metal oxides of the metal oxide material 110 are selected to have a switchable wettability when exposed to an energy activation step. In certain aspects, the metal oxide may be selected from a group consisting of: titanium oxide ($TiO_2$), zinc oxide (ZnO), tin oxide ($SnO_2$), tungsten oxide ($WO_3$), vanadium oxide ($V_2O_5$), and combinations thereof. In certain aspects, the metal oxide is $TiO_2$. The metal oxides may be applied to the substrate 112 via chemical vapor deposition, physical vapor deposition, and the like to form the metal oxide material 110.

Next, at 2, the metal oxide material 110 is silanized to form a low surface energy silanized non-wettable surface 114 by applying and reacting silane precursors on the metal oxide material 110. The low surface energy silanized non-wettable surface 114 may have a first receding contact angle and overall contact angle, as described above, for example of greater than or equal to about 10°.

In certain variations, the metal oxide material 110 is silanized to form the low surface energy silanized non-wettable surface 114 as a surface coating, which forms reacting a low surface energy fluoroalkyl silane with hydroxyl groups present within and on the metal oxide material 110. In certain aspects, the low surface energy fluoroalkyl silane can be applied onto a surface of the metal oxide material 110 before a reaction is initiated and conducted. The low surface energy fluoroalkyl silane precursor may be in the form of a coating precursor that is applied to the surface. As appreciated by those of skill in the art, other conventional components may be included in the coating precursor, so long as they do not significantly affect the wettability of the surface coating formed. Such conventional components may include solvents, carriers, antioxidants, anti-foaming agents, stabilizers, or other standard additives, like flow additives, rheology modifiers, adhesion promoters, and the like. The low surface energy fluoroalkyl silane in the precursor can be applied to the surface of the metal oxide material 110 by using any conventional coating technique including vapor phase deposition, dip coating, flow coating, spin coating, roll coating, curtain coating and spray coating.

In one example, a surface of the metal oxide material 110 is treated via a vapor-phase deposition of a low surface energy fluorine-containing silane, such as a fluoroalkyl silane, to form a coating (low surface energy silanized non-wettable surface 11) thereon. The coating comprising a fluoroalkyl silane reacted with hydroxyl groups on a surface of the metal oxide material 110 can be considered to be deep fluorosilanization via vapor deposition. Thus, in such variations, the coated surface comprises a low surface energy fluoroalkyl silane having a surface tension of less than or equal to about 35 mN/m that has reacted with hydroxyl groups on the metal oxide material 110. In certain aspects, the coated surface consists essentially of a low surface energy fluoroalkyl silane having a surface tension of less than or equal to about 35 mN/m reacted with hydroxyl groups on the metal oxide material 110.

In certain variations, the surface coating may comprise a layer formed by reacting a low surface energy fluorine-containing silane, such as a fluoroalkyl silane having a surface tension of less than or equal to about 25 mN/m with hydroxyl groups on the surface of the metal oxide material 110, and in certain variations, the low surface energy fluoroalkyl silane may have a surface tension of less than or equal to about 10 mN/m.

Thus, in such variations, the coated surface comprises a low surface energy fluoroalkyl silane having a surface tension of less than or equal to about 25 mN/m, optionally less than or equal to about 10 mN/m, that has reacted with hydroxyl groups on the metal oxide material 110. In certain aspects, the coated surface consists essentially of a low surface energy fluoroalkyl silane having a surface tension of less than or equal to about 25 mN/m, optionally less than or equal to about 10 mN/m, reacted with hydroxyl groups on the metal oxide material 110.

In certain aspects, where the surface wettability is hydrophobic and oleophobic (e.g., omniphobic), the low surface energy silanized non-wettable coated surface 114 has a ratio of fluorine to oxygen of greater than or equal to about 2. In certain aspects, greater than or equal to about 60% of the hydroxyl groups on the surface of the metal oxide material 110 are reacted with the low surface energy fluoroalkyl silane. By way of example, the hydrophobic and oleophobic surface coating may be formed by reacting a low surface energy fluoroalkyl silane selected from a group consisting of: heptadecafluoro-1,1,2,2-tetrahydrodecyl triethoxysilane, heptadecafluoro-1,1,2,2-tetrahydrodecyl trichlorosilane, heptadecafluoro-1,1,2,2-tetrahydrooctyl trichlorosilane, tridecafluoro-1,1,2,2-tetrahydrooctyl triethoxysilane, and combinations thereof.

At 3, a mask 118 defining one or more select regions 120 (e.g., openings of a predetermined shape) is placed over the low surface energy silanized non-wettable surface 114. Then, actinic radiation, such as ultraviolet (UV) radiation, or plasma treatment, is directed towards the mask 118 and reaches the low surface energy silanized non-wettable surface 114 through the openings defined by the one or more select regions 120 in the mask 118. One suitable UV radiation that may be used for activation may have a wavelength of 254 nm. Where the size of the features desired is less than 50 nm, block-copolymer nanolithography (BCNL) can be used to activate the surface to form monodisperse regions. BCNL is more suitable for such nanoscale features, because the inherent diffraction limit of light precludes the use of common photolithographic techniques.

After the activation, the mask 118 is removed at 4 to form the template 122, leaving one or more wettable surface regions 124 that have been activated by exposure to the actinic radiation or plasma treatment. The activation of the metal oxide material 110/low surface energy silanized non-wettable surface 114 thus creates the wettable surface regions 124. The wettable surface regions 124 thus define a pattern in the non-wettable surface 114 on the surface of the template 122. In certain aspects, the wettable surface regions 124 have a second receding contact angle of 0° to less than or equal to about 5° (as described above), optionally 0° to less or equal to about 1° for polar and non-polar liquids, which are capable of being wetted by and receiving polar and non-polar liquid compositions to form layers of multiphasic microparticles via the WETS process of the present disclosure.

A first region (e.g., wettable surface region 124 of the template 122) has a first surface energy, while a second region (e.g., non-wettable surface region 114 of the template 122) has a second surface energy. In certain variations, a difference between the first surface energy and the second surface energy is greater than or equal to about 10 mN/m, optionally greater than or equal to about 20 mN/m, optionally greater than or equal to about 30 mN/m, optionally greater than or equal to about 40 mN/m, optionally greater than or equal to about 50 mN/m, and in certain variations, equal to about 52 mN/m.

The first wettable region of the template may have a first surface energy of greater than or equal to about 55 mN/m, optionally greater than or equal to about 60 mN/m, optionally greater than or equal to about 65 mN/m, optionally greater than or equal to about 67 mN/m, and in certain variations, optionally greater than or equal to about 70 mN/m. The second non-wettable region of the template may have a first surface energy of less than or equal to about 25 mN/m, optionally less than or equal to about 20 mN/m, optionally less than or equal to about 15 mN/m, and in certain variations, optionally less than or equal to about 10 mN/m. In one variation, a surface energy of the first region (e.g., wettable domains) is greater than or equal to about 60 mN/m, while a surface energy of the second region (e.g., non-wettable domains) is less than or equal to about 20 mN/m. In another variation, the surface energy of the first region (e.g., wettable domains) is greater than or equal to about 65 mN/m, while a surface energy of the second region (e.g., non-wettable domains) is less than or equal to about 15 mN/m.

By way of non-limiting example, in one embodiment, a surface energy of the first region (e.g., wettable domains) is about 67 mN/m, while a surface energy of the second region (e.g., non-wettable domains) is about 15 mN/m. Thus, the difference in surface energy between wettable and non-wettable regions is about 52 mN/m. In certain aspects, even more than a difference in surface energy, absolute values of surface energy of both wettable and non-wettable domains or regions govern the ability to preferentially assemble liquids within the wettable domains.

Table 1 lists many of the different polar and non-polar liquids and polymer solutions that have demonstrated wettability engendered self-assembly within patterned surfaces (including both wettable surface regions 124 and non-wettable surface regions 114 of an exemplary template 122 comprising a surface having titanium oxide ($TiO_2$) silanized with (heptadecafluoro-1,1,2,2-tetrahydrodecyl)trichlorosilane (HDFTS), by way of non-limiting example. Advancing and receding contact angles are also listed for all liquids on both the wettable and non-wettable regions of the patterned surfaces. All the polymer solutions used for contact angle measurements are 15 wt. % solutions.

TABLE 1

| | Non-Wettable Surface Region | | Wettable Surface Region | |
|---|---|---|---|---|
| Liquids | Advancing Contact Angle ($\theta_A$) | Receding Contact Angle ($\theta_R$) | Advancing Contact Angle ($\theta_A$) | Receding Contact Angle ($\theta_R$) |
| Water | 120° | 112° | <10° | 0° |
| Dimethylformamide (DMF) | 76° | 66° | <10° | 0° |
| Toluene | 72° | 62° | <10° | 0° |
| Ethanol | 50° | 38° | 0° | 0° |
| Hexane | 47° | 33° | 0° | 0° |
| Acetone | 62° | 47° | 0° | 0° |
| Methanol | 52° | 39° | 0° | 0° |
| Isopropanol | 56° | 42° | 0° | 0° |
| Tetrahydrofuran (THF) | 66° | 53° | 0° | 0° |
| Chloroform | 64° | 51° | 0° | 0° |
| Propylene glycol monomethyl ether acetate (PGMEA) | 66° | 57° | 0° | 0° |
| Epoxy negative photoresist SU-8 | 68° | 55° | 0° | 0° |
| Polyethylene glycol diacrylate (PEGDA) | 85° | 72° | <10° | 0° |
| AK 225 (fluorinated solvent) | 28° | 14° | 0° | 0° |
| Hexadecane | 66° | 53° | 0° | 0° |
| Poly(sodium 4-styrenesulfonate) (PSS)-water | 108° | 97° | <10° | 0° |

TABLE 1-continued

| Liquids | Non-Wettable Surface Region | | Wettable Surface Region | |
|---|---|---|---|---|
| | Advancing Contact Angle ($\theta_A$) | Receding Contact Angle ($\theta_R$) | Advancing Contact Angle ($\theta_A$) | Receding Contact Angle ($\theta_R$) |
| Polyvinylidene fluoride (PVDF)-DMF | 72° | 59° | <10° | 0° |
| Polystyrene (PS)-Toluene | 72° | 58° | <10° | 0° |
| Poly(methyl methacrylate) (PMMA)-Toluene | 70° | 57° | <10° | 0° |
| Sugar-Water | 112° | 99° | <10° | 0° |
| PMMA-DMF | 73° | 60° | <10° | 0° |
| PMMA-AK 225 | 32° | 17° | 0° | 0° |
| PVDF-Acetone | 66° | 52° | 0° | 0° |
| Polydimethylsiloxane (PDMS) | 30° | 15° | 0° | 0° |
| Polyvinylalcohol (PVA)-Water | 108° | 96° | <10° | 0° |
| SU-8-PGMEA | 68° | 56° | 0° | 0° |
| Polyisobutylene (PIB)-Hexane | 50° | 32° | 0° | 0° |
| PEGDA-DMF | 78° | 68° | <10° | 0° |
| SU-8-DMF | 70° | 59° | <10° | 0° |
| PVA-Ethanol | 52° | 37° | 0° | 0° |
| PIB-THF | 53° | 39° | 0° | 0° |
| PMMA-Chloroform | 58° | 42° | 0° | 0° |

Figure 6:
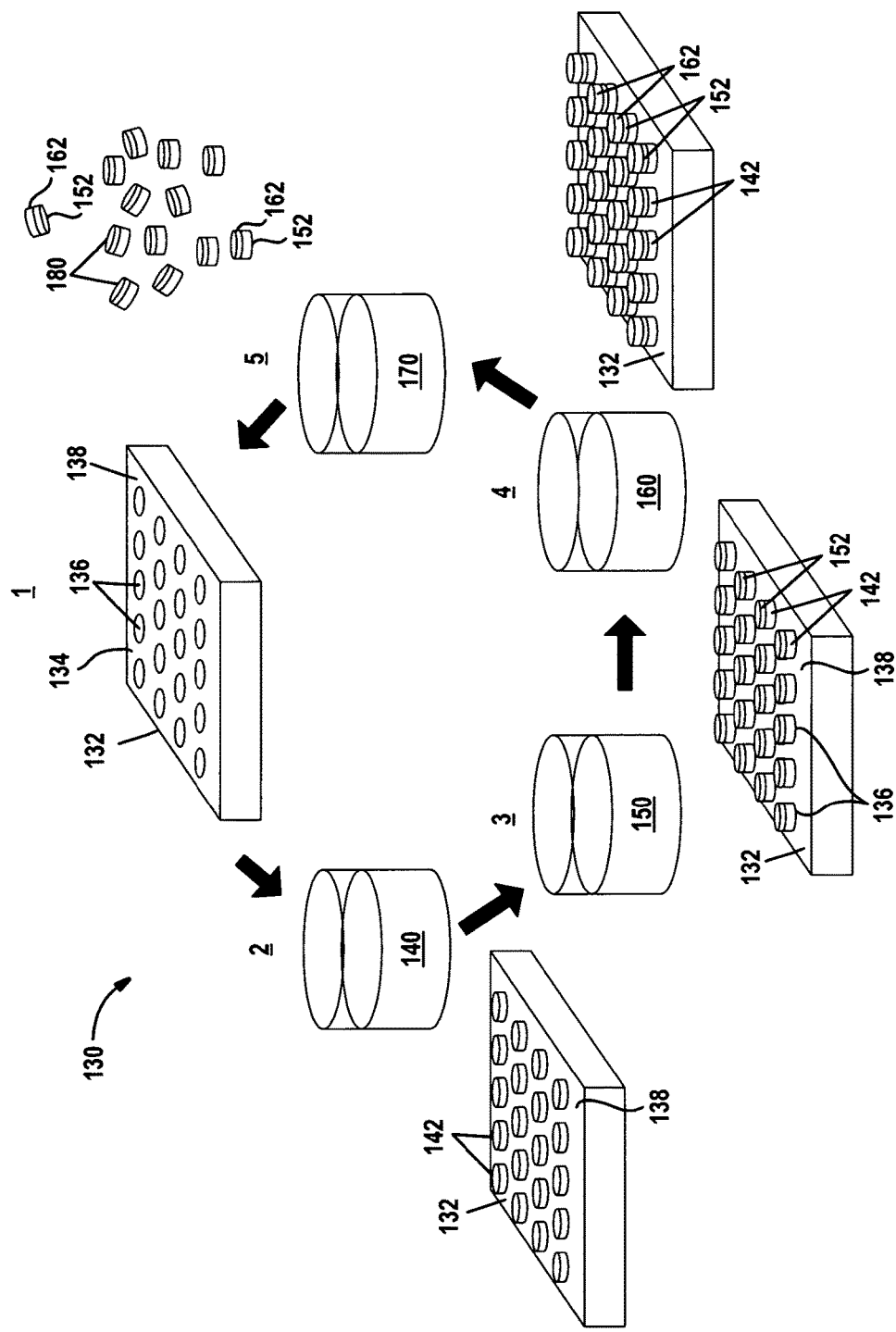
FIG. 6 shows a schematic of a process for forming multiphasic particles in accordance with certain aspects of the present disclosure.

In other aspects, the present disclosure provides methods for forming multiphasic microparticles. An exemplary WETS process 130 in accordance with certain aspects of the present disclosure is shown in FIG. 6. As shown at 1, a template 132 is used that has a patterned surface 134 defining one or more first wettable regions 136 patterned on a surface defining second non-wettable regions 138. Where a plurality of wettable regions 136 are present on the patterned surface 134, such wettable regions 136 are preferably noncontiguous, discrete regions that do not contact other adjacent wettable regions 136. Stated in another way, each wettable region 136 is physically separated from other wettable regions 136 by non-wettable regions 138. Such a patterned configuration on the surface of a template permits formation of discrete particles via the WETS process 130.

In certain aspects, the first wettable regions 136 may have a first receding contact angle of less than or equal to about 5° or any of those described previously above, so that they are wettable to polar and non-polar liquids. The second non-wettable regions 138 may have a second receding contact angle of greater than or equal to about 10°, making it non-wettable to polar and non-polar liquids.

Thus, in the WETS process 130, a first liquid composition 140 is applied to the patterned surface 134 of the template 132 at Step 2. The first liquid composition 140 can be applied to the surface 134 of the template 132 by using any conventional coating technique that enables rolling of or removal of the first liquid composition 140 (e.g., by gravitational or rotational/centrifugal forces) from the surface 134, including dip coating, flow coating, spin coating, and spraying (e.g., at an angle to permit rolling of the liquid precursor off of the surface). Such application techniques introduce a driving force, either rotational forces or gravitational forces to facilitate removal of the excess first liquid composition 140 from the surface 134 of template 132. In certain variations, the first liquid composition 140 is applied to the surface 134 of the template 132 by using a dip coating process, where the patterned surface 134 of template 132 is immersed in a container holding the first liquid composition 140 and then removed. The first liquid composition 140 may be selected to have a kinematic viscosity of greater than or equal to about $0.01 \times 10^{-6}$ m$^2$/sec to less than or equal to about $1,000 \times 10^{-6}$ m$^2$/sec, and optionally at greater than or equal to about $0.5 \times 10^{-6}$ m$^2$/s to less than or equal to about $100 \times 10^{-6}$ m$^2$/s at 40° C.

The first liquid composition 140 remains in the first regions 136, but does not wet the second regions 138, which remain dry. The materials in the first liquid composition 140 after drying preferentially self-assemble within the wettable domains (first wettable regions 136). The first liquid may comprise one or more materials that form the release layer, as well as one or more carriers or solvents, which may be volatilized or evaporated in a drying process. Depending on the carrier(s) or solvent(s), the drying process may occur within seconds to several minutes, for example, from greater than or equal to about 5 seconds to less than or equal to about 10 minutes, optionally greater than or equal to about 10 seconds to less than or equal to about 5 minutes, and optionally greater than 15 seconds to less than or equal to about 1 minute. The drying process may further include applying heat, reduced pressure, air movement, or other conventional techniques to expedite drying. In this manner, a solid or semi-solid release layer 142 is formed over the first regions 136.

By way of example, the materials present in the first liquid composition 140 for forming the release layer 142 may be soluble or disintegrate in a treatment agent that comprises specific solvent or solvents, while the materials forming other layers of the multiphasic particle are not soluble in that treatment agent (solvent or solvents). In this manner, the release layer 142 serves as a sacrificial layer that will eventually be removed from the template 132 by exposure to the solvent(s), as will be described further below.

Suitable materials for forming the solid or semi-solid release layer 142 may include poly(sodium 4-styrenesulfonate) (PSS) or sugars (e.g., sucrose, glucose, fructose, and the like), which may be present in the first liquid composition 140 as an aqueous solution comprising water and optionally other polar solvents.

At Step 3, a second liquid composition 150 is applied over the release layer 142. The application process may be the same as those described above for the first liquid composition 140 and in certain variations, may be dip coating of the patterned surface 134 of template 132 having the release layer 142 formed thereon within a receptacle holding the second liquid composition 150 and then removing the template 132. In certain variations, a critical velocity for the dip coating process may be greater than or equal to about 0.1 cm/second to less than or equal to about 1 cm/second. The second liquid composition 150 remains in the first wettable regions 134, but is repelled from the second non-wettable regions 138. The second liquid composition 150 may be selected to have a kinematic viscosity of greater than or equal to about $0.01 \times 10^{-6}$ m$^2$/sec to less than or equal to about $1,000 \times 10^{-6}$ m$^2$/sec, and optionally at greater than or equal to about $0.5 \times 10^{-6}$ m$^2$/s to less than or equal to about $100 \times 10^{-6}$ m$^2$/s at 40° C.

The second liquid composition 150 may comprise one or more materials that form a first layer 152, as well as one or more carriers or solvents, which may be volatilized or evaporated in a second drying process. The second liquid composition may comprise polymer solutions, particle dispersion, or polymer solutions with dispersants, such as inorganic microparticles or nanoparticles or functional organic molecules.

Depending on the carrier(s) or solvent(s), the second drying process may occur within seconds to several minutes, for example, from greater than or equal to about 5 seconds to less than or equal to about 10 minutes, optionally greater than or equal to about 10 seconds to less than or equal to about 5 minutes, and optionally greater than 15 seconds to less than or equal to about 1 minute. The second drying process may further include applying heat, reduced pressure, air movement, or other conventional techniques to expedite drying, as discussed above. Furthermore, in certain aspects, the first layer 152 may be annealed by heating to slightly above the glass transition temperature of the polymers contained therein. The annealing can facilitate adhesion with the underlying release layer 142. When heat is applied via the second drying process, the drying and annealing may occur concurrently or they may be conducted as separate steps.

Thus, the second liquid composition 150 forms a first layer 152 that is a solid or semi-solid disposed over the release layer 142 in the first wettable regions 136. The materials present in the second liquid composition 150 for forming the release layer 152 preferably are not soluble, do not disintegrate in the presence of, and/or are stable in the presence of the specific treatment agent solvent or solvents that will eventually be used to remove the release layer 142. Notably, in certain variations, the second liquid composition may comprise one or more polymer precursors, such as curable or crosslinkable polymer precursors. Thus, curing, crosslinking, or polymerizing the second composition forms a layer that is stable in the presence of subsequent solvents or liquid medium applied thereto. Aside from being insoluble, stable, or otherwise inert in the presence of the treatment agent for removing the sacrificial release layer 142, suitable materials for forming the solid or semi-solid first layer 152 are not limited to any particular materials. The second liquid composition 150 may comprise one or more carriers or solvents. The second liquid composition 150 also optionally comprises one or more polymers or polymer precursors (e.g., reactive monomers, oligomers, and the like) and/or one or more particles.

In certain aspects, the one or more solvents or carriers in the first or second liquid compositions may be selected from: water, dimethylformamide (DMF), toluene, alkanes, including hexane, hexadecane, ketones, including acetone, alcohols, including methanol, ethanol, and isopropanol, tetrahydrofuran (THF), chloroform, toluene, ethers, fluorinated solvents, such as 1,1-Dichloro-2,2,3,3,3-pentafluoropropane sold as Asahiklin™ AK-225, hexafluorobenzene, and any combinations thereof, by way of non-limiting example.

In other aspects, the polymer or precursor materials in the second liquid composition 150 may be polymers or polymer precursors (e.g., reactive monomers, oligomers, and the like). Examples of polymer or polymeric precursors that form the layers may be selected from the following non-limiting group: epoxy negative photoresist SU-8, poly(sodium 4-styrenesulfonate) (PSS), polyvinylidene fluoride (PVDF), polystyrene (PS), acrylates and methacrylates, such as poly(methyl methacrylate) (PMMA), polydimethylsiloxane (PDMS), polyvinylalcohol (PVA), polyisobutylene (PIB), polyethylene glycol diacrylate (PEGDA), poly(lactide-co-glycolide) (PLGA), polyelectrolytes, and combinations thereof.

In other variations, the second liquid composition 150 may comprise particles, such as silicon dioxide, magnetite, and gold nano-particles, by way of non-limiting example.

The liquid composition may also comprise common known additives, such as surface-active agents, surfactants, stabilizers, colorants, antioxidants, antifoaming agents, and the like.

It should be noted that the WETS process 130 is not limited like conventional layer-by-layer processes, which must employ alternating layers of materials having opposing charges. While the WETS process 130 may include materials of opposing charges in distinct layers, such as polyelectrolytes or charged particles, the process does not require and is not restricted to selection of materials with such opposite charges in each respective layer. Thus, in certain aspects, the first layer 152 is formed from precursors in the second liquid composition 150 that are neutral in charge.

The first layer 152 is selected so that it is insoluble, not disintegrated, or stable in the presence of the treatment agent that is used to remove release layer 142. In one variation, the release layer 142 may be selected to be soluble or disintegrated in an aqueous medium comprising water, while the first layer 152 may be selected to be water insoluble. Further, the first layer 152 is selected to be insoluble, nonreactive, or stable by the components (e.g., solvent(s) or carrier medium) in a third liquid composition 160 that will be applied over it.

Next as shown at 4, the third liquid composition 160 is thus applied over the first layer 152, where the third liquid composition 160 remains in the first wettable regions 136 of surface 134, but does not wet the second non-wettable regions 138. The third liquid composition 160 may have the same viscosity within the same ranges as the second liquid composition 150. The third liquid composition 160 has a distinct chemical composition from the second liquid composition 150, but may have solvents and carriers and polymer or precursor materials selected from the same exemplary materials previously listed in the context of the second liquid composition 150.

The third liquid composition 160 thus undergoes a third drying process and forms a second layer 162 that is a solid or semi-solid. The second layer 162 is disposed over the first layer 152. The application process may be the same as those described above for the first and second liquid compositions 140, 150 and in certain variations, may be dip coating of the patterned surface 134 of template 132 having the release layer 142 and first layer 152 formed thereon within a receptacle holding the third liquid composition 160. In certain variations, a critical velocity for the dip coating process may be greater than or equal to about 0.1 cm/second to less than or equal to about 1 cm/second. After immersing the patterned surface 134, the template 132 may be removed from the third liquid composition 160 and the third drying process may be conducted. Depending on the carrier(s) or solvent(s), the third drying process may occur within seconds to several minutes, for example, from greater than or equal to about 5 seconds to less than or equal to about 5 minutes, optionally greater than or equal to about 10 seconds to less than or equal to about 2 minutes, and optionally greater than 15 seconds to less than or equal to about 1 minute. The third drying process may further include applying heat, reduced pressure, air movement, or other conventional techniques to expedite drying, as discussed above.

In certain aspects, the first layer 162 may be annealed by heating to slightly above the glass transition temperature of the polymers contained therein. The annealing can facilitate adhesion with the underlying first layer 152. When heat is applied via the third drying process, the drying and annealing may occur concurrently or they may be conducted as separate steps.

In certain aspects, the template 132 may be exposed to heat after applying the second liquid composition 150 over the release layer 142 and after applying the third liquid composition 160 over the first layer 152. Notably, where a curable or crosslinkable polymer precursor is used in any of the first liquid composition 140, second liquid composition 150, and third liquid composition 160, concurrently or after drying, the surface 134 of template 132 may be subjected to energy or other treatment to facilitate curing, cross-linking, or polymerization (e.g., heat, actinic radiation, electron beam energy). Also, an annealing step may be formed on each layer to enhance adhesion with the underlying layer.

The second layer 162 is selected so that it is insoluble, not disintegrated, or otherwise stable in the treatment agent that is used to remove release layer 142. For example, in embodiments where the release layer 142 is soluble or disintegrated in an aqueous medium comprising water, like the first layer 152, the second layer 162 is selected to be water insoluble or stable in the presence of water. Otherwise, suitable materials for forming the solid or semi-solid second layer 162 are not limited to any particular materials. In certain aspects, the third liquid composition 160 comprises one or more carriers or solvents. The third liquid composition 160 also comprises one or more polymers or polymer precursors (e.g., reactive monomers, oligomers, and the like) and/or one or more particles, such as those discussed previously above in the context of the second liquid composition 150. The second layer 162 may be formed of a polymer precursor material that can be cured or crosslinked to form a layer that is stable in the presence of subsequent solvents or liquid medium applied thereto. In certain variations, the second layer 162 is formed from precursors in the third liquid composition 160 that are neutral in charge.

At 5, the first layer 152 and the second layer 162 are removed from the surface 134 of the template 132 by removing the release layer 142. The removing process includes applying a liquid treatment agent 170, which comprises one or more solvents or other materials that dissolve or disintegrate the release layer 142. The applying process may be any of those described above in the context of the first liquid composition 140, including dip coating within the treatment agent 170, which permits soaking of the surface 134 for a predetermined duration. For example, in one variation, the release layer 142 comprises poly(sodium 4-styrenesulfonate) (PSS), so the treatment agent 170 comprises water, which dissolves or disintegrates the release layer 142.

Heating or agitation, such as stirring of the liquid treatment agent 170 or sonication, may also be employed to facilitate dissolving or disintegration of the release layer 142. After the release layer 142 is removed, a plurality of free multiphasic microparticles 180 is formed that includes at least the first layer 152 and the second layer 162. Thus, the materials from the liquids applied to the surface (e.g., polymer or particles) preferentially self-assemble within the wettable domains of the template to make multiphasic particle assemblies with controlled geometries and compositions via the multiple depositions steps in accordance with certain aspects of the present disclosure. These multiphasic assemblies can then be released from the template in order to create the multiphasic particles. Thus, by using a simple application process like dip coating, the shape, composition, modulus, and dimensions of the produced particles can be highly controlled.

Notably, the WETS process 130 shown in FIG. 6 is simplified, but additional liquid compositions and layers may be applied or alternatively, the application steps with the first and second liquid compositions 150, 160 may be repeated to form more than two layers within the multiphasic microparticles 180. Thus, the applying of the second liquid composition 150 and the applying of the third liquid composition 160 may be repeated sequentially to form an alternating pattern comprising a plurality of first layers 152 and a plurality of second layers 162 in certain variations of processes according to the present teachings. In certain other variations, while not shown, the process may include applying at least a fourth liquid composition over the second layer 162, where the fourth liquid composition remains in the first region 136 and forms a third layer (not shown) that is a solid or semi-solid.

After 5, the release layer 142, first layer 152, and second layer 162 are all removed from the surface 134 of the template 132. The first wettable regions 136 are thus exposed again and the template 132 may be reused in a subsequent multiphasic particle formation process (e.g., starting again at Step 1). The surface 134 of template 132 may be cleaned before reuse. Templates have been readily reused (in excess of 20 times) for fabricating new batches of multiphasic particles, enabling a rapid, inexpensive, waste-free (significant when fabricating particles that encapsulate expensive biomolecules and drugs) and easily reproducible method for large-scale manufacturing of multiphasic particles. The methods of the present disclosure may be employed to form a wide range of wettable regions/domain sizes.

In certain aspects, the methods of the present disclosure contemplate fabricating multiphasic particles comprising polymers or inorganic materials. For example, in certain variations, a first layer may comprise polyethylene glycol diacrylate (PEGDA) and the second layer may comprise SU-8. In other variations, a first layer may comprise poly (sodium 4-styrenesulfonate) (PSS) and the second layer may comprise poly(vinylidene fluoride). In yet other aspects, a first layer may comprise poly(sodium 4-styrenesulfonate) (PSS), the second layer may comprise SU-8 and a third layer may comprise polystyrene (PS), by way of example. Such layer combinations are non-limiting and exemplary for purposes of illustration.

In certain other aspects, the methods of the present disclosure contemplate fabricating multiphasic particles from liquid compositions comprising charged polymers like polyelectrolytes (PEL), so that the layers may have opposite charges. A template having one or more first wettable regions and one or more second non-wettable regions like those described previously above is used. In this process, a first composition is applied to the first wettable regions of the template to form a solid or semi-solid release layer. The first composition may comprise poly(styrene-co-4-vinylpyridine), by way of non-limiting example.

Next, a second liquid composition comprising a first polyelectrolyte having a first charge is applied to the template surface having the release layer, for example, by exposure to the second liquid composition for approximately 10 minutes. Such a first polyelectrolyte may be polystyrene sulfonate (PSS), which is negatively charged. The template surface may then be rinsed, for example, via a water rinse for about 30 seconds. A first layer comprising the first polyelectrolyte, here PSS, is formed on the template surface over the poly(styrene-co-4-vinylpyridine) release layer. Then, the template is exposed to a third liquid composition comprising a second polyelectrolyte of an opposite charge from the first polyelectrolyte. The second polyelectrolyte may be poly (allylamine hydrochloride) (PAH), which is positively charged. The template may be exposed to the third liquid composition for approximately 10 minutes. The template surface may then be rinsed, for example, via a water rinse for about 30 seconds. A second layer comprising the second polyelectrolyte, here PAH, is formed on the template surface over the first PSS layer formed on the poly(styrene-co-4-vinylpyridine) release layer. The poly(styrene-co-4-vinylpyridine) can then be removed via application of a treatment comprising the solvent chloroform. FIGS. 17A-17C show SEM images of different biphasic particles formed from layered PSS/PAH polyelectrolytes having circular, square, and hexagonal cross-sectional shapes.

Notably, the polyelectrolyte can be any charged species, including without limitation, poly(styrene sulfonate) (PSS), poly(allylamine hydrochloride) (PAH), poly(diallyldimethylammonium chloride) (PDDA), chitosan (CH), poly(vinyl alcohol), aluminosilicate clay (montmorillonite), ionic polymers, for example, polylysine, oligonucleotides, polyacetylamine, collagen, alginate, carageenan, fibronectin, gelatin, extra-cellular matrix, poly(ethyleneimine) (PEI), poly aniline, polyacrylic acid, polylactic acid, and compositions containing cellulose, for example.

Thus, in certain variations the first layer 152 and second layer 162 of the multiphasic microparticle 180 respectively comprise at least one of a polymer or a particle. The first and second liquid compositions 150, 160 are compositionally distinct from one another and thus form compositionally distinct phases/layers (first layer 152, second layer 162). The multiphasic microparticles 180 formed by such processes may have any of the dimensions described previously above.

Each layer of the multiphasic microparticle may have a thickness of greater than or equal to about 5 nm to less than or equal to about 50 µm. In certain variations, the process provided herein provides the ability to form a plurality of multiphasic micro- or nano-particles that are monodisperse. Monodisperse generally refers to size distributions that deviate less than about 20%, optionally less than about 15%, optionally less than about 10%, optionally less than about 5%, and in some aspects, less than about 1%. In certain embodiments, typical particle sizes (average diameters) produced via the processes described in the present disclosure, range from greater than or equal to about 20 nm to less than or equal to about 10,000 nm (10 µm), optionally greater than or equal to about 30 nm to less than or equal to about 3,000 nm (3 µm), and in certain aspects, optionally greater than or equal to about 50 nm to less than or equal to about 1,000 nm (1 µm).

Precise control over the geometry and chemistry of multiphasic (monophasic, biphasic or Janus, tri-phasic, quadphasic and the like) micro- and nano-particles is of significant importance for a wide range of applications including drug delivery, vaccines and inhalation biotherapeutics, biological sensors, optical devices, and nanomotors. Further, the present technology provides the ability to develop precisely designed particles (building blocks) that can assemble in a preprogrammed manner to yield desired structures and properties. Further, the multiphasic particles formed in accordance with certain aspects of the present disclosure can be designed to be anisotropic, where the alignment and orientation of the phases avoids any isotropic or uniform distribution/orientation through the particle.

In certain aspects, the present disclosure provides a multiphasic microparticle that has a first layer defining a first phase and a second layer defining a second phase. The first layer is stacked on the second layer, so that the first layer defines a first major lateral dimension and the second layer defines a second major lateral dimension. The first major lateral dimension and the second major lateral dimension are perpendicular to a major dimension (e.g., the longest dimension) defined the multiphasic microparticle. In certain aspects, the major dimension may be any of those described above in the context of the major longitudinal dimension. For example, the major dimension may be less than or equal to about 1 µm. The multiphasic microparticle may have any of the aspect ratios discussed previously above. In certain aspects, the multiphasic microparticle has an aspect ratio of less than or equal to about 50.

In some embodiments, the first layer may extend laterally across and be exposed along peripheral external surfaces of the multiphasic microparticle, while the second layer likewise extends laterally across and is exposed along the peripheral external surfaces of the multiphasic microparticle. In other variations, the multiphasic microparticle comprises at least one additional phase. In certain variations, the first layer and the second layer are formed of uncharged neutral materials. In other variations, the first layer and the second layer may comprise one or more charged materials, although such materials are not necessarily present in contrast to the layer-by-layer processes that require layers of materials of opposite charges to be deposited sequentially. Thus, in certain variations, the charged material may be a charged polymer (like polyelectrolytes (PEL)) or could be a charged or non-charged neutral particle, which can be deposited in any order within the microparticle.

Multiphasic particles can thus be made according to the present technology with a wide variety of materials, including inorganic and organic materials, which can be dispersed, dissolved, or carried in a solvent or liquid medium. Specifically, polymers, such as biodegradable or non-biodegradable polymers, biocompatible polymers, or natural polymers can be used, as are well known in the art. Some non-limiting examples of these polymers include poly(lactide-co-glycolide) (PLGA), polyethylene glycol diacrylate (PEGDA), poly(styrene sulfonate) (PSS), poly(allylamine hydrochloride) (PAH), poly(diallyldimethylammonium chloride) (PDDA), and chitosan (CH).

In certain aspects, at least one phase of the multiphasic particle comprises at least one active component or ingredient. As appreciated by one of skill in the art, the first phase and the second phase (or additional distinct phases) can optionally include active ingredients that are the same or different from one another. Thus, in certain aspects, the multiphasic particle comprises a first phase having at least one active ingredient and a second distinct phase having at least one distinct active ingredient. For example, where a multiphasic particle comprises a first phase and a second distinct phase, the first phase optionally comprises one or more first active ingredients and the second phase optionally likewise comprises one or more second active ingredients. When present, one or more of the first active ingredients of the first phase can be distinct from the one or more second active ingredients of the second phase. Thus, the first phase may comprise at least one distinct active ingredient from the second phase. Multiple phases of the particle may each respectively comprise at least one active ingredient and in some cases a plurality of distinct active ingredients. In other aspects, one or more of the distinct phases of the multiphasic particle may have a common active ingredient. The first and second phases (or additional phases) may contain one or more of the same active ingredients or different active ingredient cocktails (i.e., plurality or mixture of active ingredients).

In certain aspects, the multiphasic particle optionally comprises a bioactive or pharmaceutically active ingredient, such as exclusive or generic drugs, or combinations thereof.

In accordance with certain aspects of the present disclosure, the multiphasic particle can be used in a wide variety of biofunctional or bioactive applications. A "bioactive" material or agent refers to a chemical substance, such as a small molecule, macromolecule, metal ion, or the like, that causes an observable change in the structure, function, optical function, or composition of a cell when a cell is exposed to such a substance. Examples of observable changes include increased or decreased expression of one or more mRNAs, increased or decreased expression of one or more proteins, phosphorylation of a protein or other cell component, inhibition or activation of an enzyme, inhibition or activation of binding between members of a binding pair, an increased or decreased rate of synthesis of a metabolite, increased or decreased cell proliferation, changes in optical properties, and the like. In certain aspects, the multiphasic particles may serve as drug delivery vehicles that deliver active ingredients to a target, in some embodiments, to tissue or an organ of an organism. The drug delivery may include various types of administration, including by infusion or injection (intravenous, intramuscular, subcutaneous, intracutaneous, intraperitoneal, and the like). The compositions can also be administered orally, transdermally, intranasally, or via other mucous membranes. Such nanoparticle-based therapeutics can be administered orally as a pill or an inhalant. Nanoparticles delivered desirably have a very particular shape, size and composition in order to enter the blood stream or target the area of disease. For example, it has been observed that particles within a size range of 10 nm to 100 nm exhibit high tumor accumulation through Enhanced Permeation and Retention (EPR) effect. Further, elongated particles and discoidal particles exhibit enhanced circulation times and higher tumor accumulation compared to their spherical counterparts, Similarly, in certain studies, rod-shaped particles have been shown to exhibit better tumor targeting efficiency, than spherical particles. Thus, higher efficiency therapeutics may be achieved with the use of multiphasic nanoparticles prepared in accordance with certain aspects of the present disclosure that are designed to have the desired predetermined shape (such as elongated, discoidal, or rod-shaped particles), size and characteristics to target specific organs, disease areas or other areas of the body.

In certain variations, the multiphasic micro- or nanoparticles may be administered in a vaporized stream to a patient/organism to deliver active ingredients orally or intranasally, for example for vaccines and inhalation biotherapeutics. Traditional vaccines are difficult and time-consuming to produce and must be kept in carefully controlled conditions which make distribution to developing countries difficult. Thus, there has been recent interest in nanoparticle-based vaccine. Use of nanotechnologies in vaccines and therapeutics lead to higher reproducibility and better mechanical and chemical stability properties. Thus, multiphasic nanoparticles prepared in accordance with the present disclosure can thus carry and deliver drugs for treatment of diseases like cancer and diabetes, but can also be used in detection of disease. In other aspects, the multiphasic particles provide binding to certain target regions or cells in an organism to modify optical or physical properties to improve diagnostic procedures.

Further, such multiphasic particles can be used in biological and chemical sensors, as well as in optical devices and nanomotors, by way of non-limiting example. Nanoparticles may also be integrated into biosensors for improved sensing capabilities.

By way of example, a smooth, low surface energy, silanized, titanium dioxide ($TiO_2$) surfaces is prepared in accordance with the methods described above that possesses finite receding contact angles ($\theta_R$) for both water and different low surface tension liquids (including fluorinated liquids). The smooth, low surface energy, silanized metal oxide surface is then patterned via an activation step to form high surface energy domains ($\theta_R=0$) of different shapes and sizes. Such surfaces serve as templates to engender the self-assembly of liquid solutions, including both aqueous and organic polymer solutions and dispersions.

To fabricate a WETS template in accordance with certain aspects of the present disclosure, a 5 nm thin film of titanium dioxide ($TiO_2$) is deposited onto silicon wafers through e-beam evaporation. Next, the $TiO_2$ surface is exposed to (heptadecafluoro-1,1,2,2-tetrahydrodecyl)trichlorosilane (HDFTS) vapors at 100° C. for 30 minutes. Then, the silanized $TiO_2$ surfaces are exposed to deep ultraviolet radiation (UV, 254 nm) for 90-120 minutes through a quartz photomask possessing any desired pattern. Irradiating the silanized $TiO_2$ surface with deep UV light (254 nm) serves as an activation step that forms the patterned templates on the surface. Upon deep UV irradiation, the surface energy of $TiO_2$ surfaces in the unmasked regions increases significantly due to the photo-catalytic cleavage of the $TiO_2$-silane bond, also referred to as exhibiting switch wettability after activation. This simple fabrication process provides a non-wettable surface patterned with wettable domains that are defined by the openings in the mask geometry.

When such templates are dip-coated with a polymer solution (or dispersion), the liquid preferentially wets and self-assembles within the patterned wettable domains. Upon evaporation of the solvent, the polymer (or particles from a dispersion) deposits within the patterned wettable high surface energy domains, conforming to the shape and size of the wettable regions. Such liquids may be assembled within the patterned wettable high surface energy domains via spin- or spray-coating of the liquid precursors, as well. For example, the surface of the template can be dip coated with 15 wt. % polystyrene sulfonate (PSS) or 30 wt. % sugar solutions in water to form a solid or semi-solid sacrificial release layer by permitting the water to evaporate from the surface (leaving solid PSS or sugar).

Subsequently, the template with the release layer formed thereon may be dip coated with other desired liquids, such as other polymer solutions. To demonstrate the fabrication of multiphasic polymer particles using the WETS technique, poly(sodium 4-styrenesulfonate) (PSS; using PSS in water solution) is first deposited within wettable domains (see FIG. 7A showing a fluorescent micrograph of a sacrificial release layer comprising PSS), followed by poly(vinylidene fluoride) (PVDF; using PVDF in dimethylformamide solution) on top of PSS (see FIG. 7B) and finally polystyrene (PS; using PS in toluene solution) on top of PVDF and PSS (see FIG. 7C). After depositing each polymer layer, the surfaces are annealed by heating to slightly above the glass transition temperature of the polymers to ensure good adhesion between the layers. The sequential deposition of polymers is confirmed, one on top of another, using fluorescence microscopy and atomic force microscopy height measurements (see FIGS. 7A-7C and the corresponding insets). Additional layers can be stacked within the wettable domains from other polymer solutions, as long as the solvents do not adversely affect (dissolve or disintegrate) the earlier deposited underlying polymer layers.

The assembled particles were released from the template by dissolving the sacrificial PSS or sugar sacrificial release layer in water. For self-assembly of amphiphilic particles, 1 mL of biphasic SU-8-PEGDA particles suspension in water ($5 \times 10^5$ particles/mL) is added to a flat glass cuvette (Lab-Tek II chambered glass) containing 1 mL of perfluorodecalin. The particles are allowed to settle and assemble at the water-perfluorodecalin interface under agitation using a vibration generator (3B Scientific).

The projected shape and size of the multiphasic assemblies (PSS-PVDF-PS) can be precisely controlled by utilizing different patterned surfaces, each possessing the desired geometry as a template (see FIGS. 7D-7E). The complex nature of the wettable region patterning can be controlled by the predetermined pattern of openings in the mask used during the activation process. As shown, FIG. 7D shows a patterned template with a PS polymer applied as a layer in the wettable surface regions defining a logo with the word "NATURE." FIG. 7F shows the deposition within monodisperse 10 μm domains of a sacrificial release layer comprising PSS, a first layer comprising PVDF, and a second layer comprising PS in the following order: PSS-PVDF-PS. FIG. 7G shows the assembly of PS, on top of SU-8 (commercially available from MicroChem Corp, Epoxy series), on top of PSS within nanoscale (e.g., 700 nm) wettable domains or regions.

To engender assembly of polymers within nanoscale wettable domains or regions (having diameters of 700 nm and 25 nm respectively), non-wettable surfaces patterned with wettable $TiO_2$ nano domains (as shown in FIGS. 8A, 8E, 10A, and 10E) as templates. First, these templates are dip-coated with a sacrificial polymer layer. Here, PSS (15 wt. % solution in water) and sugar layers (30 wt. % solution in water) are used as sacrificial layers for templates possessing 700 nm and 25 nm wettable domains, respectively (see FIGS. 8B, 8F, 10B, 10F). Next, the substrates are dip-coated with SU-8 and cross-linked using UV radiation (365 nm). Subsequently, the substrates are dip-coated with polystyrene (molecular weight about 2000-5000 Da). This process creates polystyrene, SU-8 and sacrificial polymer layers stacked one upon another, within the wettable domains, as shown in FIGS. 8A-8H and 10A-10H. The substrates are annealed above the glass transition temperatures of the polymers after each liquid application/polymer deposition. The AFM height images (FIGS. 8A-8H, 9A-9D, 10A-10D) show an increase in height after each polymer layer deposition within the wettable domains, indicating successful depositions of polymer layers one on top of another within the wettable regions of the patterned surface of the template.

Further, FIGS. 9A-9D show variations in thickness of polymer depositions across different 700 nm $TiO_2$ wettable domains. FIGS. 9A-9B show 3-Dimensional AFM height images of multiphasic polymer assemblies shown in FIGS. 8C and 8D, respectively. FIGS. 9C-9D show height scan profiles of the different polymer assemblies shown in FIGS. 9A and 9B, respectively. The thickness t of the patterned domains is an average value across 30 domains. The variation in thickness across the domains is about ±1 nm for bi-phasic particles with two layers (PSS-SU-8) and about ±2 nm for tri-phasic particles with three layers (PSS-SU-8-PS). This highlights the uniformity in thicknesses of layers for the particles fabricated using the WETS technique according to certain aspects of the present technology.

The thickness (t) of the liquid or polymer solution film deposited within the wettable domains of a patterned surface is dependent on the width of the wettable domain (W) and the capillary number ($Ca=\mu V/\gamma_{LV}$) for dip-coating. Here μ is the viscosity of the liquid composition (polymer solution) and V is the dip-coating velocity. As noted above, the thickness of the polymer solution deposited within the wettable domain is given by $t=kWCa^{1/3}$ where k is a proportionality constant. After the solvent has evaporated, the thickness of the polymer layer deposited within the wettable surface regions can be approximated as $t=k\phi WCa^{1/3}$, where ϕ is the volume fraction for the polymer in the solution. The thicknesses predicted using this approach match well with the experimental thickness measurements (as shown in FIG. 7I) for different polymer solutions deposited within wettable domains, possessing a range of different sizes (25 nm to 50 μm).

Using this understanding, it is possible to directly control the specific thickness of each individual layer within the multiphasic particles to within a few nm of any desired value, as reflected by the thicknesses of the layers shown in FIGS. 9A-9D and discussed above.

Furthermore, the WETS technique according to certain aspects of the present disclosure can also be employed on the sub-50 nm length scale. FIG. 7H shows the assembly of layers: PS on top of SU-8, which is on top of sugar, each sequentially deposited within patterned 25 nm wettable regions of the template. The templates with 25 nm wettable domains may be formed utilizing block-copolymer nanolithography (BCNL). As noted above, BCNL is used to fabricate these monodisperse (having an approximate diameter of about 25 nm) wettable regions, because the inherent diffraction limit of light precludes the use of common photolithographic techniques. BCNL is a scalable alternate approach that utilizes molecular self-assembly processes to generate regular nanoscopic patterns, for example of about 5 nm to about 50 nm, in size.

FIGS. 12A-12C are SEM images of various released, bi-phasic, micro- and nano-particles, demonstrating the monodispersity of biphasic particles fabricated using the inventive WETS technique. For example, FIG. 12A shows monodisperse square-shaped PEGDA-SU-8 multiphasic particles having an average diameter of about 50 μm. FIG. 12B shows monodisperse circular-shaped PEGDA-SU-8 multiphasic particles having an average diameter of about 10 μm. FIG. 12C shows monodisperse circular-shaped PEGDA-SU-8 multiphasic particles having an average diameter of about 25 nm. The average value for the particle dimensions "d" shown in the images is an average over at least 100 particles. This highlights the monodispersity or uniformity in the size of the particles fabricated using the processes according to the present teachings.

In certain aspects, the methods of the present disclosure may include forming multiphasic particles by utilizing cross-linkable oligomers in the liquid compositions during the WETS formation process. The cross-linkable oligomers offer the freedom to deposit multiple layers using the same polymer solution without any detrimental effects (dissolution or disintegration) of the already deposited layers. Here, the first cross-linkable oligomer is selected to be hydrophobic (SU-8) and the second cross-linkable oligomer is selected to be hydrophilic (poly(ethyleneglycol)diacrylate, (PEGDA)) in order to impart amphiphilicity to the cross-linked multiphasic particles.

To fabricate these amphiphilic particles, first PSS patterned templates (see, e.g., FIG. 7A) are dip-coated with SU-8 followed by cross-linking with UV irradiation (365 nm). Next, the template having the cross-linked SU-8 layer is dip-coated with a mixture of PEGDA and its cross-linker (Darocur™1173), which is also cross-linked with UV irradiation (365 nm) after it is applied. This process results in bi-phasic amphiphilic particle assemblies deposited on top of a PSS release layer within the patterned wettable regions. The amphiphilic particles are subsequently removed from the wettable regions of the surface of the templates by dissolving the PSS sacrificial layer in a treatment agent of water (see FIG. 11A). By changing the volume fraction of the cross-linker, the modulus of each individual phase or layer can be easily controlled within the amphiphilic particles. The ability to precisely control the modulus and shape of the fabricated multiphasic particles is particularly important for drug carrier applications to provide enhanced circulation times and to enable particle accumulation within specific target sites.

FIGS. 11A-11I show multi-phasic particles fabricated using the WETS technique according to certain aspects of the present disclosure. FIGS. 11A-11I are SEM images of released bi-phasic amphiphilic particles of different sizes and shapes (removed from the template by dissolution or disintegration of the sacrificial release layer) formed in accordance with certain aspects of the present disclosure. More specifically, FIGS. 11A-11F show SEM images of bi-phasic amphiphilic particles comprising polymer layers of SU-8 (dyed red as the lower layer) and PEGDA (dyed blue shown as the upper phase) released from a template having a hexagonal cross-sectional shape (FIG. 11A), a square cross-sectional shape (FIG. 11B), a complex "M" cross-sectional shape (FIG. 11C), and circular cross-sectional shapes (FIGS. 11D, 11E and 11F). The top insets in FIGS. 11D-11F show cross-sectional SEM images of the multiphasic particles clearly show the deposition of alternating SU-8 and PEGDA layers on top of a sacrificial layer of PSS formed on the template (before the particles are released and removed from the template), as shown in the insets of FIGS. 11D-11F. FIG. 11G shows tri-phasic particles formed in accordance with certain aspects of the present disclosure having SU-8-PEGDA-SU-8 layers. FIG. 11H depicts a hybrid multiphasic particle formed with both organic and inorganic layers. The hybrid particles are composed of SU-8 and SiO$_2$ nanoparticle layers, including a detailed image of a particle in the top inset of FIG. 11H. FIG. 11I shows biphasic polymeric nanoparticles comprising SU-8-PS layers having a diameter of about 25 nm. The top insets in FIGS. 11A-11C and 11G show corresponding 3-D stacked fluorescence confocal microscopy images of the particles before release and removal from the template. SU-8 is dyed red and forms the lower layer, while PEGDA is dyed blue and forms the upper layer in FIGS. 11A-11C. In FIG. 11G, the lower layer is SU-8 (dyed red), the middle layer is PEGDA (dyed blue), and the upper layer is SU-8 (dyed red). Scale bars for the top insets in FIGS. 11A-11C and 11G represent 100 µm. The bottom insets in FIGS. 11A-11B and 11G-11H show the corresponding AFM height images and thickness (t) of the released particles. The thickness of each layer can be independently controlled and controlled. The thickness t of the polymer layers within patterned domains is an average value across 30 domains/wettable regions.

In other variations, hexa-phasic particles (comprising 6 phases) composed of alternating layers of SU-8 and PEGDA, on top of the PSS sacrificial release layer are formed. In certain aspects, different stages of the WETS process for forming hexa-phasic particles are shown in FIG. 13A-13M. FIGS. 13A, 13C, 13E, 13G, 13I, and 13K are SEM images showing a cross section after sequential polymer depositions within a single wettable circular-shaped region (50 µm in diameter). These images distinctly show the deposition of six alternating layers of SU-8 and PEGDA at different thicknesses on top of the sacrificial PSS layer. FIGS. 13B, 13D, 13F, 13H, 13J, and 13L show high magnification images of the area indicated by the dashed red square shown in FIGS. 13A, 13C, 13E, 13G, 13I, and 13K, respectively. FIG. 13M shows released hexa-phasic particles upon the dissolution of the sacrificial PSS layer.

In this manner, the WETS technique according to certain aspects of the present disclosure allows for the fabrication of a wide variety of monodisperse multiphasic particles with precise control over the size, shape, composition, thickness, and placement of the different polymeric or inorganic phases within the particle.

The methods of the present disclosure are capable of fabricating bi-phasic, polymer nanoparticles having diameters of 25 nm or smaller (as shown in FIG. 11I) by releasing the multiphasic polymer assemblies shown in FIG. 7H. Previously, it has been extremely difficult to fabricate organic nanoparticles possessing all dimensions below 50 nm. Making particles with dimensions in the size range of 10-100 nm can be important for certain applications, for example, when particles are used as drug carriers to exhibit high circulation time in blood and provide high tumor accumulation. For example, one conventional technique developed for fabricating Janus particles of different sizes and projected shapes is known as the PRINT technique. However, this technique is incompatible with many fluorinated solvents, and cannot be used to make even single-phase particles smaller than 80 nm. Thus, although various inorganic nanoparticles, possessing different shapes, and with all dimensions below 30 nm are commercially available, even single-phase organic nanoparticles possessing similar dimensions are not. It is believed that the WETS process provided by the present teachings is the only methodology for fabricating monodisperse, multiphasic particles, especially organic multiphasic particles, of essentially any projected shape, composition, and dimensions of 25 nm or smaller.

Further, the multiple phases within the particles may be independently loaded with different cargos or ingredients to provide the particles with multi-functional capabilities. Such particles can be beneficial in developing multi-functional therapeutic systems, as they can encapsulate multiple drugs simultaneously. It is also possible for the different drugs to possess different, independently controlled release kinetics, depending on the degradation/swelling behavior of their respective encapsulant phases/materials in the target environment. In addition, some of the particle phases can be loaded with functional nanoparticles or molecules to aid in the imaging and transportation of the particles within a biological system using an external field.

For example, as shown in FIGS. 14A-14D, tri-phasic particles are integrated with three different functionalities. Here, the first phase is SU-8 loaded with magnetite nanoparticles, second phase is SU-8 loaded with a fluorescent red dye, and the third phase is a hydrogel (cross-linked PEGDA). Such tri-phasic particles can function as drug carriers that are easy to track (fluorescent imaging) and manipulate using a magnetic field to evade biological hurdles, and guide towards the target site. FIG. 14A shows a cross-sectional SEM image of a tri-functional tri-phasic particle comprising magnetic, fluorescent and hydrogel phases or layers. FIG. 14B shows a higher magnification image of the area indicated by the dashed red square shown in FIG. 14A. FIG. 14C shows a fluorescent microscope image of the tri-functional particles, released from the WETS template. FIG. 14D shows a cluster of tri-functional particles on a water surface. The particle motion is shown as the cluster is transported along the trajectory indicated by the white dashed line using an external magnetic field applied in different directions.

The two-dimensional self-assembly of the fabricated biphasic amphiphilic particles at an oil-water interface is studied here, as shown in FIGS. 15A-15C. After introducing the amphiphilic particles at the oil-water interface, a vibrating stage is used to induce in-plane movement of the particles. The frequency and amplitude of the vibrations are adjusted to bring the particles close to one another, and to break misaligned particle aggregates. The bi-phasic amphiphilic particles assembled into close packed structures with the hydrophobic phase (SU-8) dyed red and shown on the top is preferentially oriented towards the oil layer, and the hydrophilic phase (PEGDA) dyed blue shown on the bottom is oriented towards the water layer (see FIGS. 15A-15C).

FIGS. 16A-16F show time lapsed optical microscopy images of a self-assembly process for biphasic polymer particles formed in accordance with the present disclosure at an oil-water interface over a period of 10 hours. FIG. 16A is taken at 30 seconds, FIG. 16B at 2 minutes, FIG. 16C at 5 minutes, FIG. 16D at 15 minutes, FIG. 16E at 1 hour, and FIG. 16F at 10 hours. As can be seen in FIGS. 16A-16F, the assembled structures grew in size with time. This assembly of particles is driven by the minimization of interfacial free energy at the oil-water interface.

FIGS. 15A-15C show that the self-assembled close packed structures obtained are defined by the geometry (circle in FIG. 15A, square in FIG. 15B, and hexagon shapes in FIG. 15C) of the amphiphilic building blocks. These results illustrate the utility of the inventive WETS techniques for developing a variety of amphiphilic building block, important for studies on particle self-assembly, as well as, the bottom-up approaches envisioned to build various materials and devices.

The present disclosure provides new methods of fabricating a wide variety of monodisperse, multiphasic particles having anisotropic orientations in complex shapes, and sizes on the order of 25 nm or smaller, while maintaining control over the thickness, composition, and modulus of each layer/phase with the particle. A range of multiphasic, amphiphilic particles that are anisotropic in both geometry and chemistry are thus provided.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of forming multiphasic microparticles comprising:
    applying a first liquid composition to a surface of a template defining a first region having a first receding contact angle of less than or equal to about 5° for polar and non-polar liquids and a second region having a second receding contact angle of greater than or equal to about 10° for polar or non-polar liquids, wherein the first liquid composition remains in the first region and forms a release layer that is a solid or semi-solid;
    applying a second liquid composition over the release layer, wherein the second liquid composition remains in the first region and forms a first layer that is a solid or semi-solid;
    applying a third liquid composition over the first layer, wherein the third liquid composition remains in the first region and forms a second layer that is a solid or semi-solid; and
    releasing the first layer and the second layer from the template by removing the release layer from the template to create a multiphasic microparticle comprising at least the first layer and the second layer.

2. The method of claim 1, wherein the applying of the first liquid composition, the applying of the second liquid composition, and the applying of the third liquid composition are dip coating processes.

3. The method of claim 2, wherein the first liquid composition and the second liquid composition respectively have a kinematic viscosity of greater than or equal to about $0.01 \times 10^{-6}$ m$^2$/sec to less than or equal to about $1,000 \times 10^{-6}$ m$^2$/sec.

4. The method of claim 1, wherein the first region of the template has a first surface energy and the second region of the template has a second surface energy, wherein a difference between the first surface energy and the second surface energy is greater than or equal to about 10 mN/m.

5. The method of claim 1, wherein the first region of the template has a first surface energy and the second region of the template has a second surface energy, wherein a difference between the first surface energy and the second surface energy is greater than or equal to about 20 mN/m.

6. The method of claim 1, wherein the first region of the template has a first surface energy of greater than or equal to about 60 mN/m, while the second region of the template has a second surface energy of less than or equal to about 20 mN/m.

7. The method of claim 1, further comprising:
    annealing the first layer after the applying of the second liquid composition,
    annealing the second layer after the applying of the third liquid composition; or
    annealing both the first layer and the second layer after the applying of the second liquid composition and after the applying of the third liquid composition.

8. The method of claim 1, wherein the removing of the release layer occurs by exposing the template to a treatment agent that dissolves or disintegrates the release layer.

9. The method of claim 8, wherein the release layer comprises a material selected from the group consisting of: poly(sodium 4-styrenesulfonate) (PSS), sugar, and combinations thereof, and the treatment agent comprises water.

10. The method of claim 1, wherein the first liquid composition and the second liquid composition independently comprise a material selected from the group consisting of: a polymer, a polymer precursor, a particle, and combinations thereof.

11. The method of claim 10, wherein the material is selected from the group consisting of: poly(styrene sulfonate) (PSS), polyvinylidene fluoride (PVDF), polystyrene (PS), poly(methyl methacrylate) (PMMA), polydimethylsiloxane (PDMS), poly(vinyl alcohol) (PVA), polyisobutylene (PIB), epoxy-based negative photoresist SU-8, polyethylene glycol diacrylate (PEGDA), poly(styrene-co-4-vinylpyridine), poly(allylamine hydrochloride) (PAH), poly(allylamine hydrochloride) (PAH), poly(diallyldimethylammonium chloride) (PDDA), chitosan (CH), aluminosilicate clay (montmorillonite), polylysine, oligonucleotides, polyacetylamine, collagen, alginate, carageenan, fibronectin, gelatin, extra-cellular matrix, poly(ethyleneimine) (PEI), polyaniline, polyacrylic acid, polymethacrylic acid, polylactic acid, cellulose-based materials, and combinations thereof.

12. The method of claim 1, further comprising:
heating the template after the applying of the second liquid composition over the release layer;
heating the template after the applying of the third liquid composition over the first layer; or
heating after both the applying of the second liquid composition over the release layer and after the applying of the third liquid composition over the first layer.

13. The method of claim 1, further comprising crosslinking or polymerizing the first layer, the second layer, or both the first layer and the second layer.

14. The method of claim 1, wherein the applying of the second liquid composition and the applying of the first liquid composition is repeated sequentially to form an alternating pattern comprising a plurality of first layers and a plurality of second layers.

15. The method of claim 1, wherein at least one of the first liquid composition and the second liquid composition are neutral in charge.

16. The method of claim 1, further comprising applying a fourth liquid composition over the second layer, wherein the fourth liquid composition remains in the first region and forms a third layer that is a solid or semi-solid.

17. The method of claim 1, wherein the template is reusable after the releasing.

18. The method of claim 1, wherein the surface defines a plurality of first regions and a plurality of multiphasic microparticles is formed after the releasing of the first layer and the second layer, wherein the plurality of multiphasic microparticles is monodisperse and has an average diameter of greater than or equal to about 10 nm to less than or equal to about 500 μm.

19. The method of claim 1, wherein the surface of the template comprises a low surface energy fluorine-containing silane disposed over a metal oxide material.

20. The method of claim 19, wherein the metal oxide material is selected from a group consisting of: titanium oxide ($TiO_2$), zinc oxide (ZnO), tin oxide ($SnO_2$), tungsten oxide ($WO_3$), vanadium oxide ($V_2O_5$), and combinations thereof.

21. The method of claim 19, wherein the low surface energy fluorine-containing silane over the metal oxide material defines the second region and the low surface energy fluorine-containing silane over the metal oxide material is activated in at least one select region to define the first region.

22. The method of claim 19, wherein the low surface energy fluorine-containing silane is a fluoroalkyl silane selected from the group consisting of: heptadecafluoro-1,1,2,2-tetrahydrodecyl triethoxysilane, heptadecafluoro-1,1,2,2-tetrahydrodecyl trichlorosilane, heptadecafluoro-1,1,2,2-tetrahydrooctyl trichlorosilane, tridecafluoro-1,1,2,2-tetrahydrooctyl triethoxysilane, and combinations thereof.

23. A method of forming multiphasic microparticles comprising:
applying a first liquid composition to a surface of a template defining a first region having a first receding contact angle of less than or equal to about 5° for polar and non-polar liquids and a second region having a second receding contact angle of greater than or equal to about 10° for polar or non-polar liquids, wherein the surface comprises a silanized metal oxide material and the first liquid composition remains in the first region and forms a release layer that is a solid or semi-solid;
applying a second liquid composition over the release layer, wherein the second liquid composition remains in the first region and forms a first layer that is a solid or semi-solid;
applying a third liquid composition over the first layer, wherein the third liquid composition remains in the first region and forms a second layer that is a solid or semi-solid; and
releasing the first layer and the second layer from the template by removing the release layer from the template to create a multiphasic microparticle comprising at least the first layer and the second layer.

24. The method of claim 23, wherein the metal oxide material is selected from a group consisting of: titanium oxide ($TiO_2$), zinc oxide (ZnO), tin oxide ($SnO_2$), tungsten oxide ($WO_3$), vanadium oxide ($V_2O_5$), and combinations thereof.

25. The method of claim 23, wherein the silanized metal oxide material comprises a low surface energy fluorine-containing silane disposed over the metal oxide material that defines the second region and the low surface energy fluorine-containing silane disposed over the metal oxide material is activated in at least one select region to define the first region.

26. The method of claim 23, wherein the silanized metal oxide material comprises a low surface energy fluorine-containing silane selected from the group consisting of:
heptadecafluoro-1,1,2,2-tetrahydrodecyl triethoxysilane, heptadecafluoro-1,1,2,2-tetrahydrodecyl trichlorosilane, heptadecafluoro-1,1,2,2-tetrahydrooctyl trichlorosilane, tridecafluoro-1,1,2,2-tetrahydrooctyl triethoxysilane, and combinations thereof.

* * * * *